United States Patent [19]
Hatsuya et al.

[11] Patent Number: 5,342,840
[45] Date of Patent: Aug. 30, 1994

[54] CYCLOPROPANE DERIVATIVE

[75] Inventors: Satoshi Hatsuya; Takaaki Sekiyama; Takashi Tsuji; Satoshi Iwayama; Masahiko Okunishi, all of Kawasaki, Japan

[73] Assignee: Ajinomoto Co., Inc., Tokyo, Japan

[21] Appl. No.: 846,615

[22] Filed: Mar. 5, 1992

[30] Foreign Application Priority Data

Mar. 5, 1991 [JP] Japan ................. 3-123239
Jul. 24, 1991 [JP] Japan ................. 3-184709

[51] Int. Cl.$^5$ ............ A61K 31/52; C07D 473/00
[52] U.S. Cl. .................. 514/262; 514/261; 544/276; 544/277
[58] Field of Search .......... 544/276, 277; 514/261, 514/262

[56] References Cited

U.S. PATENT DOCUMENTS

| | | | |
|---|---|---|---|
| 3,923,792 | 12/1975 | Albrecht et al. | 544/317 |
| 4,016,267 | 4/1977 | Albrecht et al. | 544/317 |
| 4,548,818 | 10/1985 | Kjellin et al. | 544/273 |
| 4,617,304 | 10/1986 | Ashton et al. | 544/276 |
| 4,644,001 | 2/1987 | Kjellin et al. | 544/267 |
| 4,782,062 | 11/1988 | Tolman et al. | 544/276 |
| 4,859,680 | 8/1989 | Ashton et al. | 544/317 |
| 4,918,075 | 4/1990 | Zahler et al. | 544/277 |
| 4,988,703 | 1/1991 | Norbeck et al. | 544/276 |
| 5,064,961 | 11/1991 | Bisacchi et al. | 544/276 |
| 5,126,345 | 6/1992 | Slusarchyk et al. | 544/317 |

OTHER PUBLICATIONS

Tai-Shun Lin, J. Med. Chem. 1987, 30, 440–444.
Wallace T Ashton, J. Med. Chem. 1988, 31, pp. 2304-2315.

*Primary Examiner*—Cecilia Tsang
*Attorney, Agent, or Firm*—Oblon, Spivak, McClelland, Maier & Neustadt

[57] ABSTRACT

A cyclopropane derivative of formula (I)

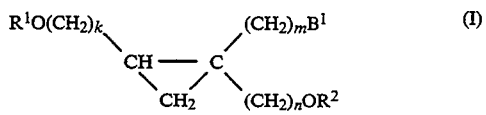

wherein $B^1$ is a purine or pyrimidine residue, $R^1$ and $R^2$ are, independently, hydrogen or a protecting group for hydroxyl and each of k, m and n represents, independently, an integer of 1 or 2 is useful for its antiviral effect.

13 Claims, No Drawings

CYCLOPROPANE DERIVATIVE

BACKGROUND OF THE INVENTION

1. Field of the Invention

The invention relates to a cyclopropane derivative, to methods for its manufacture, and to pharmaceutical compositions including it. The derivative is, in particular, for anti-viral use and the invention includes the use of the derivative in the manufacture of a medicament for anti-viral use, as well as the use of the derivative in the treatment of viral diseases.

2. Description of the Prior Art

There is as yet no drug available which is satisfactory, in terms of its efficacy and safety, for the treatment of many viral diseases. It is, therefore, highly desirable that improved anti-viral drugs should be developed.

Many nucleic acid-related compounds have an anti-viral activity, and some of them are used as anti-viral drugs. Among these are, acyclovir, gancoclovir, and azidothymidine.

Known compounds which are closely related to, or are derivatives of nucleic acid bases, and some of which have anti-viral activity include those disclosed in the following references:

Norbeck, U.S. Pat. No. 4,988,703 issued Jan. 29, 1991, discloses cyclopropyl-substituted purine and pyrimidine analogues which are useful as antiviral agents.

Ashton, U.S. Pat. Nos. 4,617,304 and 4,859,680 issued Oct. 14, 1986 and Aug. 22, 1989, respectively, disclose ((hydroxymethyl) cyclopropyl) methyl)-substituted purine and pyrimidine analogues which are useful as anti-viral agents.

Albrecht, U.S. Pat. Nos. 4,016,267 and 3,923,792 issued Apr. 5, 1977 and Dec. 2, 1975, respectively, disclose cyclopropyl-, cyclopropylmethyl- and cylclopentyl-substituted nucleoside analogues which are useful as antibacterial agents.

Kjellin, U.S. Pat. Nos. 4,644,001 and 4,548,818, issued Feb. 17, 1987 and Oct. 22, 1985, respectively, disclose cyclopropyl-, cyclobutyl- and cylclopentyl-substituted purine and pyrimidine analogues which are useful for treating obstructive airway disease or cardiac disease.

Temple, J. Med. Chem. 5, 866(1962), discloses cyclopropyl-substituted purine analogues which are useful for treating human epidermal carcinoma.

Masoliver, Spanish patent No. ES51989, published Mar. 16, 1984, discloses cyclopropyl-substituted purine analogues.

None of the above-mentioned references discloses or suggests the compounds of the present invention.

SUMMARY OF THE INVENTION

According to a first aspect of the present invention there is provided a cyclopropane derivative of formula (I), a salt, optical or geometric isomer thereof:

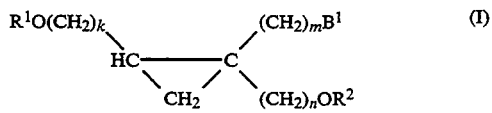

wherein $B^1$ represents a purine residue or pyrimidine residue, $R^1$ and $R^2$ represent a hydrogen atom or a protective group for the hydroxyl group and may be the same or different, and each of k, m and n represents independently, an integer of 1 or 2.

The present inventors have discovered that such compounds have an anti-viral effect.

DETAILED DESCRIPTION OF THE INVENTION

Examples of suitable purine residues in the formula (I) are, for example, an adenine residue, a guanine residue, a xanthine residue, a hypoxanthine residue, a 2-amino-6-chloropurine residue, a 2,6-diaminopurine residue or a 2-aminopurine residue. Preferably, the purine residue is a purine-9-yl group.

Examples of suitable pyrimidine residues are, for example, a thymine residue, a uracil residue, such as fluorouracil or a cytosine residue. Preferably, the pyrimidine residue is a pyrimidine-1-yl group.

Examples of suitable protecting groups $R^1$ and $R^2$ will be apparent to those of skill in the art. Examples include benzyl, tetrahydropyranyl, acyl, and silyl. The acyl group may be an alkylacyl group or an arylacyl group. Specific examples of silyl group are trimethylsilyl and t-butyldimethylsilyl.

Specific examples of the cyclopropane derivatives of the invention are shown below.

9-[1'α, 2'β-bis(hydroxymethyl)cyclopropan-1'β-yl]methylguanine,

9-[1'α, 2'α-bis(hydroxymethyl)cyclopropan-1'β-yl]methylguanine,

9-[1'α, 2'β-bis(hydroxymethyl)cyclopropan-1'β-yl]methyladenine,

9-[1'α, 2'α-bis(hydroxymethyl)cyclopropan-1'β-yl]methyladenine,

9-[1'α, 2'β-bis(hydroxymethyl)cyclopropan-1'β-yl]methyl-2-amino-6-chloropurine,

9-[1'α, 2'α-bis(hydroxymethyl)cyclopropan-1'β-yl]methyl-2-amino-6-chloropurine,

9-[1'α, 2'β-bis(hydroxymethyl)cyclopropan-1'β-yl]methylhypoxanthine,

9-[1'α, 2'α-bis(hydroxymethyl)cyclopropan-1'β-yl]methylhypoxanthine,

1-[1'α, 2'β-bis(hydroxymethyl)cyclopropan-1'β-yl]methylthymine,

1-[1'α, 2'α-bis(hydroxymethyl)cyclopropan-1'β-yl]methylthymine,

1-[1'α, 2'β-bis(hydroxymethyl)cyclopropan-1'β-yl]methylcytosine,

1-[1'α, 2'α-bis(hydroxymethyl(cyclopropan-1'β-yl]methylcytosine,

1-[1'α, 2'β-bis(hydroxymethyl)cyclopropan-1'β-yl]methyluracil,

1-[1'α, 2'α-bis(hydroxymethyl)cyclopropan-1'β-yl]methyluracil,

1-[1'α, 2'β-bis(hydroxymethyl)cyclopropan-1'β-yl]methyl-5-fluorouracil,

1-[1'α, 2'α-bis(hydroxymethyl)cyclopropan-1'β-yl]methyl-5-fluorouracil,

9-[1'α, 2'α-bis(hydroxymethyl)cyclopropan-1'β-yl]methyl-2,6-diaminopurine,

9-[1'α, 2'β-bis(hydroxymethyl)cyclopropan-1'β-yl]methyl-2,6-diaminopurine,

9-[1'α, 2'α-bis(hydroxymethyl)cyclopropan-1'β-yl]methyl -2-aminopurine,

9-[1'α, 2'β-bis(hydroxymethyl)cyclopropan-1'β-yl]methyl -2-aminopurine,

9-[1'α, 2'α-bis(acetoxymethyl)cyclopropan-1'β-yl]methylguanine,

9-[1'α, 2'β-bis(acetoxymethyl)cyclopropan-1'β-yl]methylguanine,

9-[1'α, 2'α-bis(benzoyloxymethyl)cyclopropanyl-1'β-yl]methylguanine,
9-[1'α, 2'β-bis(benzoyloxymethyl)cyclopropanyl-1'β-yl]methylguanine,
9-[1'α, 2'α-bis(acetoxymethyl)cyclopropan-1'β-yl]methyladenine,
9-[1'α, 2'β-bis(acetoxymethyl)cyclopropan-1'β-yl]methyladenine,
9-[1'α, 2'α-bis(benzoyloxymethyl)cyclopropan-1'β-yl]methyladenine,
9-[1'α, 2'β-bis(benzoyloxymethyl)cyclopropan-1'β-yl]methyladenine,
9-[1'α, 2'α-bis(acetoxymethyl)cyclopropanyl-1'β-yl]methyl-2-amino-6-chloropurine,
9-[1'α, 2'β-bis(acetoxymethyl)cyclopropanyl-1'β-yl]methyl-2-amino-6-chloropurine,
9-[1'α, 2'α-bis(benzoyloxymethyl)cyclopropanyl-1'β-yl]methyl-2-amino-6-chloropurine,
9-[1'α, 2'β-bis(benzoyloxymethyl)cyclopropanyl-1'β-yl]methyl-2-amino-6-chloropurine,
9-[1'α, 2'α-bis(acetoxymethyl)cyclopropanyl-1'β-yl]methylhypoxanthine,
9-[1'α, 2'β-bis(acetoxymethyl)cyclopropanyl-1'β-yl]methylhypoxanthine,
9-[1'α, 2'α-bis(benzoyloxymethyl)cyclopropanyl-1'β-yl]methylhypoxanthine,
9-[1'α, 2'β-bis(benzoyloxymethyl)cyclopropanyl-1'β-yl]methylhypoxanthine,
1-[1'α, 2'α-bis(acetoxymethyl)cyclopropanyl-1'β-yl]methylthymine,
1-[1'α, 2'β-bis(acetoxymethyl)cyclopropanyl-1'β-yl]methylthymine,
1-[1'α, 2'α-bis(benzoyloxymethyl)cyclopropan-1'β-yl]methylthymine,
1-[1'α, 2'β-bis(benzoyloxymethyl)cyclopropan-1'β-yl]methylthymine,
1-[1'α, 2'α-bis(acetoxymethyl)cyclopropan-1'β-yl]methylcytosine,
1-[1'α, 2'β-bis(acetoxymethyl)cyclopropan-1'β-yl]methylcytosine,
1-[1'α, 2'α-bis(benzoyloxymethyl)cyclopropan-1'β-yl]methylcytosine,
1-[1'α, 2'β-bis(benzoyloxymethyl)cyclopropan-1'β-yl]methylcytosine,
1-[1'α, 2'α-bis(acetoxymethyl)cyclopropan-1'β-yl]methyluracil,
1-[1'α, 2'β-bis(acetoxymethyl)cyclopropan-1'β-yl]methyluracil,
1-[1'α, 2'α-bis(benzoyloxymethyl)cyclopropan-1'β-yl]methyluracil,
1-[1'α, 2'β-bis(benzoyloxymethyl)cyclopropan-1'β-yl]methyluracil,
9-[1'α, 2'α-bis(acetoxymethyl)cyclopropan-1'β-yl]methyl-2,6-diaminopurine,
9-[1'α, 2'β-bis(acetoxymethyl)cyclopropan-1'β-yl]methyl-2,6-diaminopurine,
9-[1'α, 2'α-bis(benzoyloxymethyl)cyclopropan-1'β-yl]methyl-2,6-diaminopurine,
9-[1'α, 2'β-bis(benzoyloxymethyl)cyclopropan-1'β-yl]methyl-2,6-diaminopurine,
9-[1'α, 2'α-bis(acetoxymethyl)cyclopropan-1'β-yl]methyl-2-aminopurine,
9-[1'α, 2'β-bis(acetoxymethyl)cyclopropan-1'β-yl]methyl-2-aminopurine,
9-[1'α, 2'α-bis(benzoyloxymethyl)cyclopropan-1'β-yl]methyl-2-aminopurine,
9-[1'α, 2'β-bis(benzoyloxymethyl)cyclopropan-1'β-yl]methyl-2-aminopurine,
9-[(1'α-hydroxymethyl-2'α-hydroxyethyl)cyclopropan-1'β-yl]methylguanine,
9-[(1'α-hydroxymethyl-2'β-hydroxyethyl)cyclopropan-1'β-yl]methylguanine,
7-[1'α,2'β,-bis(hydroxymethyl)cyclopropane-1'β-yl]methylguanine,
7-[1'α,2'β-bis(hydroxymethyl)cyclopropane-1'β-yl]methylguanine,
7-[1'α,2'α-bis(hydroxymethyl)cyclopropane-1'β-yl]methyl adenine.
7-[1'α,2'β-bis(hydroxymethyl)cyclopropane-1'β-yl]methyl adenine.

The cyclopropane derivatives shown above include both racemic compounds and optically active compounds. Preferred compounds have an R configuration at one of the cyclopropane asymmetric carbons and an S configuration at the other.

As to the relative steric configurations of these compounds, when cyclopropane is considered as a flat plane, a substituent located below the flat plane is expressed as α, and a substituent above the flat plane is expressed as β.

According to a second aspect of the invention there is provided a method for the production of the cyclopropane derivative, salt or isomer of the first aspect, the method comprising at least one of the steps of:

(a) reacting a compound of formula (I) with an acid or alkali to produce a pharmaceutically acceptable salt;
(b) deprotecting a compound of formula (I) in which at least one of $R^1$ and $R^2$ is a protecting group to yield a compound of formula (I) in which each of $R^1$ and $R^2$ is hydrogen;
(c) esterifying a compound of formula (I) in which at least one of $R^1$ and $R^2$ is hydroxyl to produce a compound of formula (I) in which one or both of $R^1$ and $R^2$ are protecting groups, and preferably are acyl groups;
(d) reacting a compound of formula (XIV)

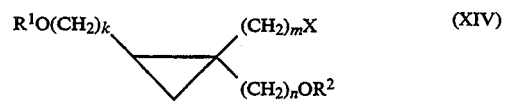

wherein $R^1$, $R^2$, k, m and n are as defined above and X is a leaving group, with an optionally protected purine or pyrimidine and then, optionally, deprotecting the product.

Compounds of the present invention in which k, m and n are 1 may be prepared by various methods, such as those represented by the following schemes. Modifications may be made to the schemes, as will be apparent to the person of skill in the art, so that compounds having any or all of k, m and n being 2 may be prepared.

SCHEME I

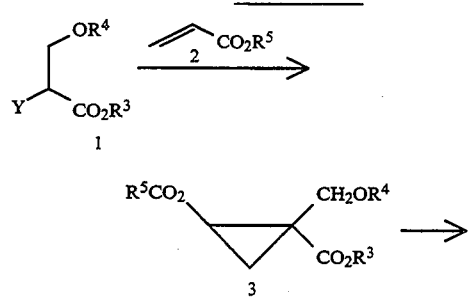

-continued
SCHEME I

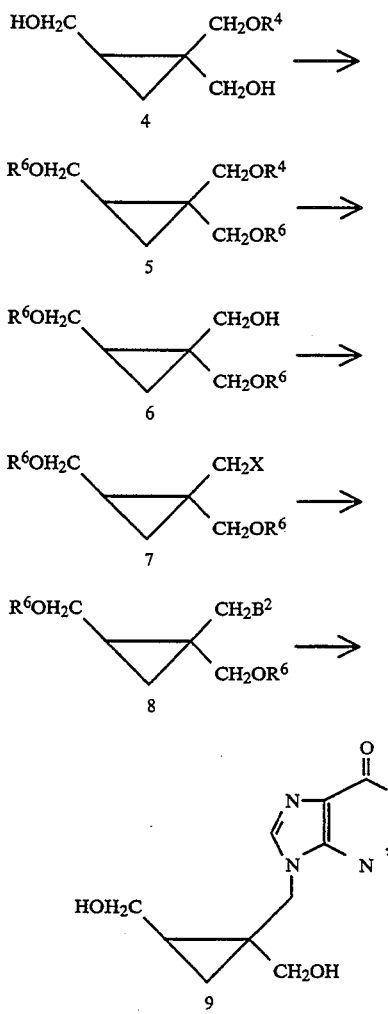

Scheme I illustrates a method for the production of a guanine derivative (formula 9). However, it will be understood that by appropriate selection of $B^2$ (in formula 8) the scheme can be used for the preparation of cyclopropane derivatives of other purines and pyrimidines.

The ester of formula 1 in which Y is Cl or Br, $R^3$ is a protective group for the carboxyl group such as methyl or benzyl and $R^4$ is a protective group for the hydroxyl group such as silyl or benzyl, is reacted with the acrylic acid ester of formula 2 in which $R^5$ is an alkyl group, in a polar solvent such as dimethylformamide in the presence of a base such as sodium hydride or potasium carbonate to obtain a compound of formula 3. The diastereomer mixture is separated by silica gel column chromatography.

Then, the ester groups of the compound of formula 3 are reduced to obtain the alcohol of formula 4. Examples of the reducing agent used at this time are lithium aluminum hydride, lithium borohydride, and sodium bis(2-methoxyethoxy)aluminum hydride (Red-Al). Then, the hydroxyl groups are protected to obtain a compound of formula 5. An acyl group is preferred as $R^6$.

$R^4$ is removed from the compound of formula 5. When $R^4$ is benzyl, it can be deprotected by hydrogenation in the presence of palladium carbon. Then, the compound 6 is provided with a leaving group, for example is converted into a tosylate, mesylate or a halide of formula 7 by using p-toluenesufonyl chloride, methanesulfonyl chloride or phosphorus tribromide in the presence of a base such as pyridine or triethylamine. X represents a leaving group such as p-toluenesulfonyloxy group, a methanesulfonyloxy group or halogen.

The compound of formula 7 is stirred with heating with a protected purine or pyrimidine. In the scheme as illustrated this is 6-benzyloxyguanine.

A polar solvent such as dimethylformamide is preferably employed. A protected guanine derivative of formula 8 results. Potassium carbonate or sodium hydride may be used as a base, and 18-crown-6 may be included to assist solvation.

The compound of formula 8 is reacted with hydrochloric acid in methanol or hydrogenated in the presence of a palladium carbon catalyst to remove the protective group and to form the guanine derivative of formula 9.

2-amino-6-chloropurine may be used as the purine in place of guanine as now described.

When 2-amino-6-chloropurine is used, the compound of formula 8 may be hydrolyzed to remove only $R^6$ to get a 2-amino-6-chloropurine derivative. This compound can be converted to a 2,6-diaminopurine derivative by treatment with ammonia. 2-aminopurine may also be used in place of guanine to give 2-aminopurine derivatives.

The compound of formula 6 may be obtained by another scheme as shown below.

SCHEME II

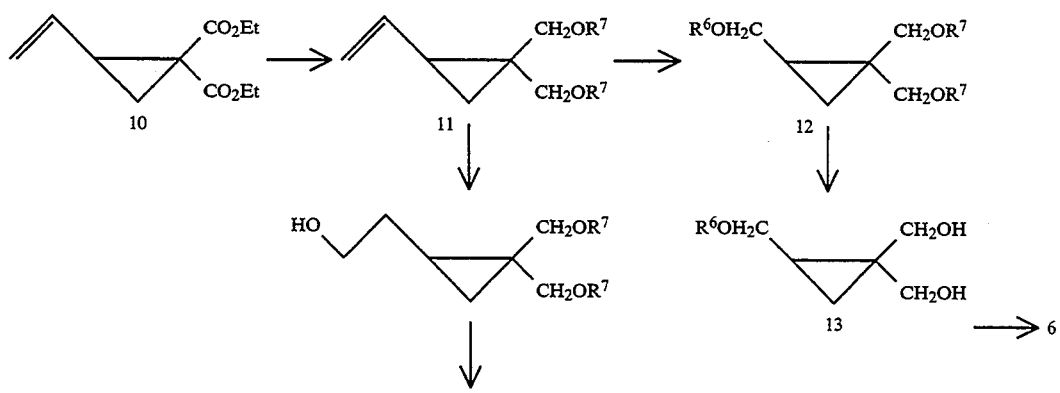

-continued
SCHEME II

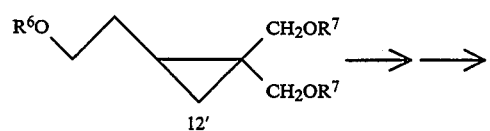
12'

The compound of formula 10 obtained by using the method described in J. Med. Chem. 31, 2304–2315 (1988) is reduced with lithium aluminum hydride, and the hydroxyl compound is protected at the hydroxyl group to obtain the compound of formula 11. At this time, the protected group $R^7$ is suitably a tert-butyldimethylsilyl group, etc. After the double bond of formula 11 is cleaved oxidatively, the resulting hydroxyl group is protected with a benzoyl, or similar group ($R^6$). Removal of the protective group $R^7$ of the resulting compound of formula (2) gives the compound of formula 13.

Protection of one of the hydroxyl groups of the compound of formula 13 gives the compound of formula 6.

The stereoisomers of the compound of formula 6 obtained by this method may be separated by means such as chromatography before use in a later reaction, or may be used as a mixture and the stereoisomers separated subsequently.

The methylene homo analogue of 12 (formula 12') can be prepared by hydroboration of 11 and used further in the same way.

The following scheme shows the alkylation of adenine. Other purines and pyrimidines may be used similarly.

SCHEME III

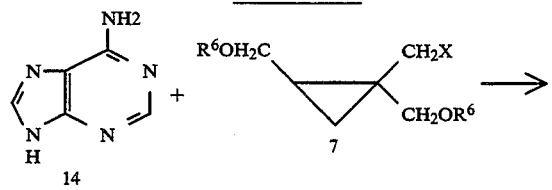

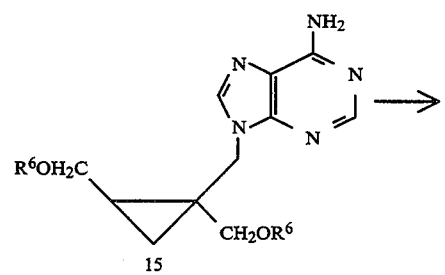

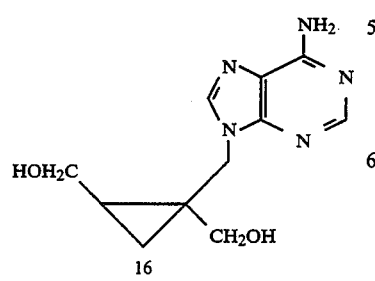

The compound of formula 7 and adenine (formula 14) are stirred with heating in the presence of a base such as sodium hydride or potassium carbonate to obtain the compound of formula 15. Then, the elimination of the protective group $R^6$ gives the compound of formula 16. If 6-chloropurine is used instead of adenine, then after alkylation the 6-position of the purine ring may be aminated with ammonia, etc. to give the compound of formula 15.

As shown by the following scheme IV, the action of adenosinedeaminase on the adenine derivative (formula 17) can give the compound of formula 18 having a hypoxanthine residue. $R^8$ may be hydrogen, or a protective group for the hydroxyl group.

The compound of formula 17 may alternatively be converted chemically utilizing nitrite salts to give 18.

SCHEME IV

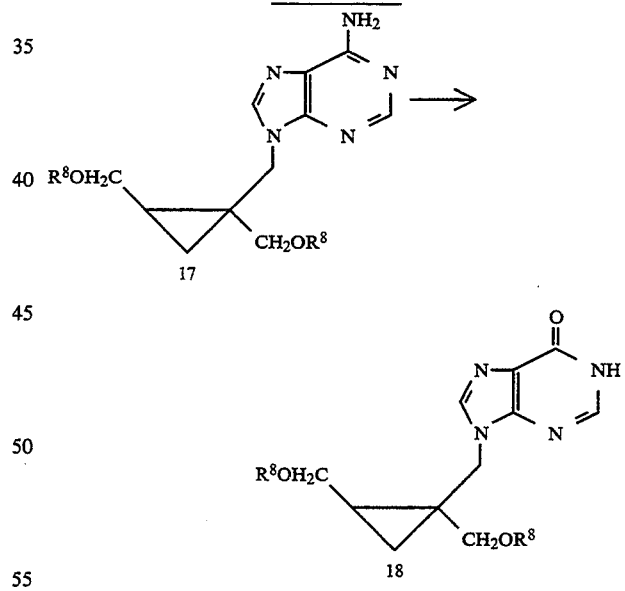

The following schemes V and VI show the alyklation of exemplary pyrimidines.

SCHEME V

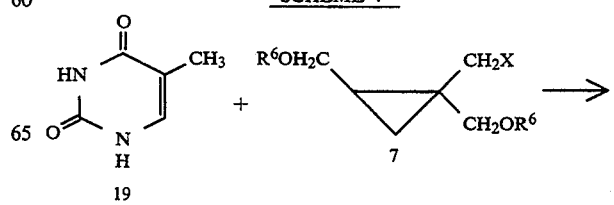

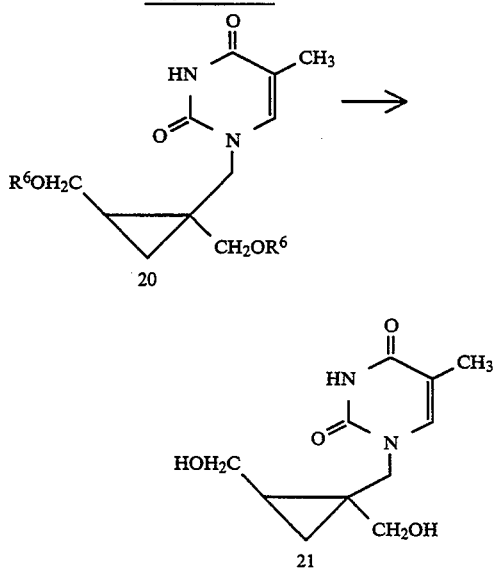

-continued
SCHEME V

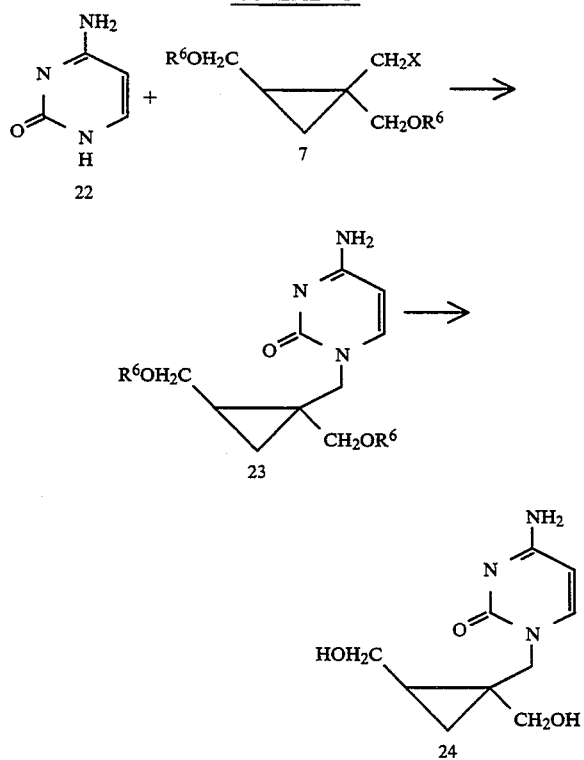

SCHEME VI

Thymine (formula 19) or cytosine (formula 22) is reacted, in the presence of base such as sodium hydride or potassium carbonate, with the compound of formula 7. In the reaction, sodium iodide may also be present. The solvent is suitably a polar solvent such as dimethyl sulfoxide or dimethylformamide. $R^6$ is a protective group for the hydroxyl group, such as a silyl group, an acyl group or a benzyl group. It may be removed in a deprotection with methanol in hydrochloric acid, or with hydrogen in the presence of a palladium carbon catalyst to obtain the thymine derivative (formula 21) or the cytosine derivative (formula 24). A uracil derivative may be used in a similar manner by using uracil instead of thymine or cytosine.

Esters of the cyclopropane derivatives can be prepared in the course of the above scheme by selecting suitable acyl protective groups in the compound of formula 6 or the alcohols such as those of formula 9, 16, 21 and 24 may be acylated with acyl halides or acyl anhydrides in the presence of base.

Stereo specific preparation of the compounds can be achieved by the method shown in the following scheme. Dialkylmalonate is reacted with epichlorohydrin in the presence of base such as sodium alkoxide in a similar manner to that described in the literature (Pirrung, M. C. et al. Helv. Chim. Acta, 72, 1301(1989)) to give the compound of formula 25. Then the lactone 25 is reduced by suitable reductant such as sodium borohydride to give a diol of formula 26. The hydroxyl groups are protected and the ester is reduced with appropriate reductant such as lithium borohydride, lithium aluminum hydride to give a single stereoisomer of compound 6 (formula 28).

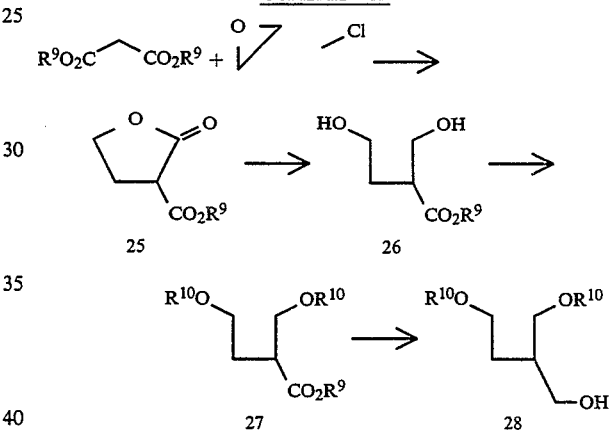

The alcohol 28 is treated in a similar manner to that shown in schemes I–VI to give one stereoisomer of the compounds of formula 9, 16, 21, 24 or of their derivatives.

Since the reaction of dialkylmalonate and epichlorohydrin proceed in a stereo specific manner as shown in the above literature, an optically pure cyclopropane derivative of formula 25 may be obtained by using optically pure epichlorohydrin. Thus, the optically pure form of one stereoisomer of the compounds of formula 9, 16, 21, 24 or of their derivatives may be obtained by utilizing the optically pure cyclopropane derivative of formula 25.

According to a third aspect of the present invention there is provided an intermediate for use in the production of a cyclopropane derivative of the first aspect, the intermediate having formula (XV).

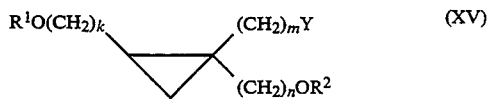

wherein Y is OH or a leaving group such as halogen, tosyl or mesyl, and $R^1$, $R^2$, k, m and n are as defined above.

The cyclopropane derivative of the first aspect of this invention may be reacted with a suitable acid to obtain a pharmaceutically acceptable salt. Acids forming such a salt may include, for example, inorganic acids such as hydrochloric acid, hydrobromic acid, sulfuric acid or phosphoric acid, acetic acid, lactic acid, citric acid, tartaric acid, maleic acid, or monomethylsulfuric acid. The salt-forming reaction may be carried out in a conventional manner.

In the case of guanine derivatives pharmaceutically acceptable salts can also be prepared by treatment with a hydroxide or alkoxide of an alkali metal in an appropriate solvent.

According to a fourth aspect of the present invention there is provided a cyclopropane derivative of the first aspect for pharmaceutical use, for example in the form of a composition comprising the cyclopropane derivative and a pharmaceutically acceptable excipient, diluent or carrier. The compound of the first aspect of this invention has anti-viral activity and is suitable for use as an anti-viral drug. Examples of viruses against which the derivative of the present invention may be useful include retroviruses such as HIV (Human Immunodeficiency Virus), herpes simplex virus, cytomegalovirus, VZV (Variella-Zoster Virus), EBV (Epstein-Barr Virus) and hepatitis virus.

When a compound according to the first aspect of this invention is used as an anti-viral drug, it may be administered parenterally, e.g. intravenously, or by an oral route or by a transdermal route. The dosage differs according to the condition, age and the route of administration to the patient, but usually it is 0.1 to 500 mg/kg/day. The present compound is preferably administered as an anti-viral drug composition mixed with a suitable formulation carrier, and, optionally with one or more other ingredients commonly included in pharmaceutical compositions. The dosage form of the composition may, for example, be an injection, tablet, granules, fine granules, powder, capsule, cream, or suppository. Examples of the formulating carrier include lactose, glucose, D-mannitol, starch, crystalline cellulose, calcium carbonate, kaolin, gelatin, hydroxypropylcellulose, hydroxypropylmethylcellulose, polyvinyl pyrrolidone, ethanol, carboxymethylcellulose, carboxymethylcellulose calcium salt, magnesium stearate, talc, acetylcellulose, white sugar, titanium oxide, benzoic acid, para-oxybenzoic acid esters, sodium acetate, gum arabic, tragacanth, methylcellulose, egg yolk, surface-active agents, simple syrup, citric acid, distilled water, ethanol, glycerol, propylene glycol, polyethylene glycol, disodium hydrogen phosphate, sodium dihydrogen phosphate, sodium phosphate, sodium chloride, phenol, thimerosal, and sodium hydrogen sulfite. The carrier and optional other ingredients may be chosen according to the intended dosage form.

The content of the effective ingredient of the present invention in the pharmaceutical composition of the invention varies greatly depending on the dosage form, and is not limited. Usually, it is 0.01 to 90% by weight, preferably 0.01 to 20% by weight, especially preferably 0.1 to 10% by weight.

Embodiments of the invention are described below, by way of example only.

EXAMPLE 1

Preparation of (±) 9-[1'α, 2'β-bis(hydroxymethyl)cyclopropan-1'β-yl]methylguanine Step 1: Production of 1,1-bis[(tert-butyldimethylsilyloxy)methyl]-2-vinylcyclopropane.

17.46 g (82.3 mol) of diethyl 2-vinyl-1,1-cyclopropanedicarboxylic acid was dissolved in 82.3 ml (82.3 mmol) of tetrahydrofuran, and 90.5ml (90.5 mmol) of a tetrahydrofuran solution of 1M lithium aluminum hydride was slowly added at 0° C., and the solution was then stirred at room temperature for 30 minutes. The solution was cooled to 0° C. and 33 ml of methanol was added. Then, 300 ml of methanol and 15 ml of water were added, and the solution was filtered using Celite. The solvent was distilled off from the filtrate and the resulting residue dissolved in dichloromethane. The solution was filtered using Celite, and the filtrate was concentrated. To 7 g of the residue (corresponding to 55 mmol of 1,1-bis(hydroxymethyl)-2-vinylcyclopropane), were added 16.48 mg (242 mmol) of imidazole and 105 ml of dimethylformamide. 18.24g (121 mmol) of tert-butyldimethylsilyl chloride was added while maintaining a temperature of 0° C., and the solution was then stirred overnight at room temperature. The dimethylformamide was distilled off, and ether and a saturated aqueous solution of sodium bicarbonate were added, and the organic layer was separated. The solvent was distilled off from the organic layer. The residue was purified by silica gel column chromatography (3% ether/hexane) to obtain 16.53 g (46.3 mmol 56%) of 1,1-bis(tert-butyldimethylsilyloxy)methyl]-2-vinylcyclopropane as a colorless oil. Proton nmr of the product was as follows:

$^1$H-NMR (CDCl$_3$) δ: 0.02 (s, 3H), 0.03 (s, 3H), 0.03 (s, 3H), 0.03 (s, 6H), 0.56 (dd, J=4.8, 4.8 Hz, 1H), 0.80 (dd, J=4.8, 8.4 Hz, 1H), 0.88 (s, 9H), 0.89 (s, 9H), 1.50 (m, 1H), 3.43 (d, J=9.9 Hz, 1H), 3.51 (d, J=10.5 Hz, 1H), 3.68 (d, J=9.9 Hz, 1H), 3.71 (d, J=10.5 Hz, 1H), 4.97 (ddd, J=0.6, 2.1, 10.2 Hz, 1H ), 5.18 ( ddd, J=O. 9, 2.1, 17.1 Hz, 1H), 5.69 (ddd, J=8.1, 10.2, 17.1 Hz, 1H).

Step 2: Preparation of 2,2-bis[(tert-butyldimethylsilyloxy)methyl]cyclopropane carbaldehyde 16.55 g (46.4 mmol) of 1,1-bis[(tert-butylsilyloxy)methyl]-2-vinylcyclopropane and 10.87 g (92.9 mmol) of 4-methylmorpholine-N-oxide were dissolved in 165 ml of 33% water/tetrahydrofuran, and 23.2 ml (2.32 mmol) of an acetone solution of 0.1M osmium tetraoxide was added. The solution was stirred for 4 hours at room temperature. The tetrahydrofuran was distilled off, and dichloromethane and a saturated aqueous solution of sodium bicarbonate were added. The organic layer was separated. The resulting organic layer was dried over anhydrous sodium sulfate, filtered and then the solvent was distilled off. 11.91 g (55.7 mmol) of sodium periodide was added to the residue, and the mixture was dissolved in 248 mg of 33% water/tetrahydrofuran. The solution was stirred overnight at room temperature. The tetrahydrofuran was distilled off and ether and a saturated aqueous solution of sodium bicarbonate were added, followed by separation of the organic layer. The resulting organic layer was dried over anhydrous sodium sulfate, filtered and the solvent was distilled off. The resulting colorless oily product was subjected to silica gel chromatography (7% ether/hexane) to obtain 13.50 g (37.7 mmol, 81%) of 2,2-bis[(tert-butyldimethylsilyloxy)methyl]cyclopropane carbaldehyde. This was obtained as a colorless oil. $^1$H-NMR in CDCl$_3$ was as follows: δ: 0.01 (s, 3H), 0.03 (s, 3H), 0.04 (s, 6H), 0.86 (s, 9H), 0.88 (s, 9H), 1.20 (dd, J=5.1, 7.8 Hz, 1H), 1.42 (dd, J=5.1, 5.1 Hz, 1H), 1.91 (ddd, J=5.1, 5.1, 7.8 Hz, 1H), 3.46 (d, J=10.2 Hz, 1H), 3.58 (d, J=11.1 Hz, 1H), 3.30 (d, J=10.2 Hz, 1H), 3.95 (d, J=11.1 Hz, 1H), 9.46 (d, J=4.5 Hz, 1H); Field desorption mass spectroscopy (FD MASS) gave a peak at m/z 301 (M+-t-Bu).

Step 3: Preparation of 2,2 -bis[(tert-butyldimethylsilyloxy)methyl]cyclopropylmethyl benzoate.

13.50 g (37.6 mmol) of 2,2-bis[(tert-butyldimethylsilyloxy)methyl]cyclopropane carbaldehyde was dissolved in 200 ml of methyl alcohol, and 3.56 g (94.0 mmol) of sodium borohydride was added at 0° C. The solution was stirred for 30 minutes at 0° C. The methyl alcohol was distilled off, and then dichloromethane and a saturated aqueous solution of ammonium chloride were added.

The resulting organic layer was separated and was dried over anhydrous sodium sulfate, filtered, and the solvent was distilled off. The resulting residue was dissolved in 200 ml of pyridine, and 6.55 ml (56.4 mmol) of benzoyl chloride was added while maintaining a temperature of 0° C. The solution was then stirred for 30 minutes at 0° C. Ice was added, and the mixture was stirred for a further 15 minutes at 0° C. Pyridine was then distilled off, and ether and a saturated aqueous solution of sodium bicarbonate were added. The resulting organic layer was separated, dried over anhydrous sodium sulfate and filtered. The solvent was distilled off. The resulting colorless oily product was purified by silica gel column chromatography to obtain 21.15 g (45.5 mmol; 66%) of 2,2-bis[(tert-butyldimethylsilyloxy)methyl]-cyclopropylmethyl benzoate. This was a colorless oil, nmr and mass spectrometry of which gave the following results:

$^1$H-NMR (CDCl$_3$) δ: 0.02 (s, 3H), 0.03 (s,6H), 0.04 (s, 3H), 0.55 (dd, J=5.1, 5.1 Hz, 1H), 0.76 (dd, J=5.1, 8.4 Hz, 1H), 0.8 (s, 18H), 1.29 (m, 1H), 3.44 (d, J=10.2 Hz, 1H), 3.63 (d, J=10.2 Hz, 1H), 6.63 (d, J=11.1Hz, 1H), 3.86 (d, J=11.1 Hz, 1H), 4.34 (dd, J=7.8, 11.7 Hz, 1H), 4.43 (dd, J=7.8, 11.7 Hz, 1H), 7.43 (m, 2H), 7.5 (m, 1H), 8.06 (m, 2H); F D MASS, m/z 464 (M+), 407 (M+-t-Bu).

Step 4: Preparation of 2,2-bis(hydroxymethyl)cyclopropylmethyl benzoate 137 ml (137 mmol) of 1N hydrochloric acid, and 683 ml of methanol were added to 21.15 g (45.5 mmol) of 2,2-bis[(tert-butyldimethylsilyloxy)methyl]cyclopropylmethyl benzoate, and the solution was stirred for 40 minutes at room temperature. The solvent was distilled off, and the resulting oily product was purified by silica gel column chromatography (4% methanol/dichloromethane) to obtain 10.91 g (45.5 mmol, 100%) of 2,2-bis(hydroxymethyl)cyclopropyl methylbenzoate. This was a colorless oil; $^1$H-NMR (CDCl$_3$) δ: 0.52 (dd, J=5.4, 5.4 Hz, 1H), 0.82 (dd, J=5.1, 8.7 Hz, 1H), 1.41 (m, 1H), 2.95 (broad s, 2H), 3.55 (d, J=11.4 Hz, 1H), 3.66 (d, J=11.4 Hz, 1H), 3.69 (d, J=12.0 Hz, 1H), 4.03 (d, J=12.0 Hz, 1H), 4.29 (dd, J=8.7, 12.0 Hz, 1H), 4.57 (dd J=6.3, 12.0 Hz, 1H), 7.44 (m, 2H), 7.56 (m, 1H), 8.04 (m, 2H); FD MASS, M/z 236 (M+).

Step 5: Preparation of (E) and (Z)-(2-benzoyloxymethyl-1-hydroxymethyl)cyclopropylmethyl benzoate.

1.06 g (4.49 mmol) of 2,2-bis(hydroxymethyl)cyclopropylmethyl benzoate was dissolved in 16 ml of pyridine, and 0.52 ml (4.49 mmol) of benzoyl chloride was added at 0° C. The solution was stirred for 40 minutes at room temperature. At 0° C., ice was added, and the solution was stirred for 5 minutes at 0° C. Pyridine was distilled off and dichloromethane and a saturated aqueous solution of sodium bicarbonate were added, followed by separation of the organic layer. The resulting organic layer was dried over anhydrous sodium sulfate and filtered. The solvent was distilled off and the resulting colorless oily product was purified by silica gel column chromatography (1–5% methyl alcohol/dichloromethane) to obtain 455 mg (1.34 mmol; 30%) of (E)-(2-benzoyloxymethyl-l-hydroxymethyl)cyclopropylmethyl benzoate, 455 mg (1.34 mmol; 30%) of (Z)-2-benzoyloxymethyl-l-hydroxymethyl)cyclopropylmethyl benzoate; Colorless oil: $^1$H-NMR (CDCl$_3$) δ: 0.68 (dd, J=5.7, 5.7 Hz, 1H), 1.04 (dd, J=5.7, 9.3 Hz, 1H), 1.57 (dddd, J=5.7, 5.7, 9.3, 9.3 Hz, 1H), 1.78 (broad s, 1H), 3.70 (d, J=12.6 Hz, 1H), 3.94 (d, J=12.6 Hz, 1H), 4.18 (dd, J=9.3, 12.0 Hz, 1H), 4.33 (d, J=11.4 Hz, 1H), 4.38 (d, J=11.4 Hz, 1H), 4.74 (dd, J=5.7, 12.0 Hz, 1H), 7.39 (m, 4H), 7.55 (m, 4H), 8.01 (m, 4H); FD MASS, m/z 341 (M++H). (Z)-(2-benzoyloxyymethyl-1-hydroxymethyl)cyclopropylmethyl benzoate, Colorless oil: $^1$H-NMR (CDCl$_3$) δ: 0.74 (dd, J=9.0, 6.0 Hz, 1H), 0.98 (dd, J=6.0, 9.0 Hz, 1H), 1.50 (dddd, J=6., 6.0, 9.0, 9.0 Hz, 1H), 1.99 (broad s, 1H), 3.41 (d, J=12.0 Hz, 1H), 3.71 (d, J=12.0 Hz, 1H), 4.28 (dd, J=9.0, 12.3 Hz, 1H), 4.29 (d, 12.3 Hz, 1H), 4.64 (dd, J=6.0, 12.3 Hz, 1H), 4.85 (d, J=12.3 Hz, 1H), 7.35 (m, 4H), 7.52 (m, 2H), 7.98 (m, 4H); FD MASS, m/z 340 (M+).

Step 6: Preparation of (Z)-[1,2-bis(benzoyloxymethyl)]cyclopropyl methyl p-toluenesulfonate 2.13 g (6.26 mmol) of (E)-(2-benzoyl-oxymethyl-2-hydroxymethyl)cyclopropylmethyl benzoate was dissolved in 64 ml of dichloromethane, and 4.59 g (37.6 mmol) of 4-(dimethylamino)pyridine was added, and the solution was stirred for 5 minutes at 0° C. Then, 3.58 mg (18.8 mmol) of p-toluenesulfonyl chloride, dissolved in 64 ml of dichloromethane was added, and the solution was stirred for 1 hour at 0° C. Dichloromethane and a saturated aqueous solution of sodium bicarbonate were added, followed by separation of the organic layer. The resulting organic layer was dried over anhydrous sodium sulfate, and filtered, and the solvent was distilled off. The resulting colorless oily product was purified by silica gel column chromatography (25–50% ethylacetate/dichloromethane) to obtain 2.59 g (5.24 mmol, 84%) of (Z)-[1,2-bis(benzoyl-oxymethyl)]cyclopropylmethyl p-toluenesulfonate. The purified product was a white solid: $^1$H-NMR (CDCl$_3$) δ: 0.81 (dd, 6.0, 6.0 Hz, 1H), 1.08 (dd, J=6.0, 8.7 Hz, 1H), 1.66 (m, 1H), 2.27 (s, 3H), 4.02 (dd, J=9.3, 12.3 Hz, 1H), 4.05 (d, J=12.0 Hz, 1H), 4.23 (d, J=12.0 Hz, 1H), 4.26 (d, J=11.1 Hz, 1H), 4.30 (d, J=11.1 Hz, 1H), 4.64 (dd, J=6.0, 12.3 Hz, 1H) 7.18 (m, 2H), 7.27–7.41 (m, 4H), 7.55 (m, 2H), 7.74 (m, 2H), 7.85 (m, 2H), 7.97 (m, 2H); F D MASS, m/z 494 (M+).

Step 7: Preparation of (±) 2-amino-6-benzyloxy-9-[1'α, 2'β-bis(benzoyloxymethyl)cyclo-propan-1'β-yl]methylpurine and (±) 2-amino-6-benzloxy-7-[1'α, 2'β-bis(benzoyloxymethyl)cyclopropan-1'β-yl]methylpurine 168 mg (0.696 mmol) of 2-amino-6-benzyloxy-purine, 167 mg (0.695 mmol) of 18-crown-6, and 96 mg (0.696 mmol) of anhydrous potassium carbonate were dissolved in 4 ml of anhydrous dimethylformamide, and the solution was stirred for 5 minutes at room temperature. 287 mg (0.58 mmol) of (Z)-[1,2-bis(benzoyloxymethyl)]cyclopropylmethyl p-toluenesulfonate in 7.5 ml of dimethylformamide was then added to the solution. The solution was stirred for 2 hours at 60° C. The solvent was distilled off, and dichloromethane and a saturated aqueous solution of sodium bicarbonate were added to separate the organic layer. The organic layer was dried over anhydrous sodium sulfate, filtered, and the solvent was distilled off. The resulting residue was purified by silica gel chromatography (2–7% methanol/dichloromethane) to obtain 199 mg (0.353 mmol, 61%) of (±) 2-amino-6-benzyloxy-9-[1'α, 2β-bis(benzoyloxymethyl)cyclopropan-1'β-yl]methylpurine, and 82.6 mg (0.147 mmol, 25%) of (±) 2-amino-6-benzyl-oxy-7-[1'α, 2'β-bis(benzoyloxymethyl)cyclopropan-1'-β-yl]methylpurine. (±2-amino-6-benzyloxy-9-[1'α, 2'β-bis(benzoyloxymethyl)cyclopropan-1'β-yl]methyl purine was obtained as a colorless oil; $^1$H-NMR (CDCl$_3$) δ: 1.05 (dd, J=6.0, 9.3 Hz, 1H), 1.15 (dd, J=6.0, 6.0 Hz, 1H), 1.74 (dddd, J=6.0, 6.0, 9.3, 9.3 Hz, 1H), 3.95 (d, J=12.3 Hz, 1H), 4.22 (d, J=15.3 Hz, 1H), 4.33 (d, J=9.3, 12.3 Hz, 1H), 4.35 (d, J=12.3 Hz, 1H), 4.57 (d, J=15.3 Hz, 1H), 4.90 (broad s, 2H), 4.92 (dd, J=6.0, 12.3 Hz, 1H), 5.47 (d, J=12.3 Hz, 1H), 5.52 (d, J=12.3 Hz, 1H), 7.30–7.39 (m, 7H), 7.47–7.57 (m, 4H), 7.83 (s, 1H), 7.92–7.98 (m, 4H); FD MASS, m/z 563 (M+). (±) 2-amino-6-benzyloxy-[1'α, 2'β-bis(benzoyloxymethyl)-cyclopropan-1'β-yl]-methylpurine was a colorless oil: $^1$H-NMR (CDCl$_3$) δ: 0.80 (dd, J=6.0, 9.0 Hz, 1H), 1.01 (dd, J=6.0, 6.0 Hz, 1H)., 1.68 (m, 1H), 6.68 (dd, J=10.5, 12.3 Hz, 1H), 3.75 (d, J=12.3 Hz, 1H), 4.21 (d, J=15.0 Hz, 1H), 4.35 (d, J=12.3 Hz, 1H), 4.52 (dd, J=4.12, 12.3 Hz, 1H), 4.73 (d, J=15.0 Hz, 1H), 5.22 (broad s, 2H), 5.35 (d, J=11.7 Hz, 1H), 5.58 (d, J=11.7 Hz, 1H), 7.27–7.56 (m, 10H), 7.83 (m,2H), 7.91 (m, 2H) 8.09 (s, 1H); F D MASS, m/z 563 (M+).

Step 8: Preparation of (±) 9-[1'α, 2'β-bis-(hydroxymethyl)cyclopropan-1'β-yl]methylguanine 42.4 mg (1.06 mmol) of sodium hydride was washed with hexane, and 8.98 ml of methyl alcohol was added. The mixture was stirred for 5 minutes. This solution was added to 199 mg (0.353 mmol) of (±) 2-amino-6-benzyloxy-9-[1'α, 2'β-bis(benzoyloxymethyl)-cyclopropan-1'β-yl]methylpurine, and the solution was stirred for 30 minutes at 40° C. 1.77 ml (1.77 mmol) of 1N hydrochloric acid was added, and the solution was stirred for 30 minutes at 50° C. The solution was cooled to room temperature, and the solvent was distilled off. The residue was purified by reverse phase C18 silica gel chromatography (0–30% methyl alcohol/water) to obtain 80.5 mg (0.303 mmol, 86%) of (±)9-[1'α, 2'β-bis(hydroxymethyl)cyclopropan-1'β-yl]methylguanine. This was obtained as a white powder; $^1$H-NMR (DMSO-D6) δ: 0.52–0.59 (m, 2H), 1.12 (dddd, J=6.0, 6.0, 8.4, 8.4, 1H), 3.03 (dd, J=4.5, 11.4 Hz, 1H), 3.15 (dd, J=4.5, 11.4 Hz, 1H), 3.47 (m, 1H), 3.72 (m, 1H), 3.99 (d, J=14.4 Hz, 1H), 4.14 (d, J=14.4 Hz, 1H), 4.64 (broad s, 2H), 7.75 (s, 2H), 10.56 (broad s, 1H); high resolution mass spectrum, calculated: $C_{11}H_{16}O_3N_5$ (M++H) m/z 266.1235, Measured: m/z 266.1244.

EXAMPLE 2

Preparation of (±) 7-[1'α, 2'β-bis(hydroxymethyl)cyclopropan-1'β-yl]methylguanine Using 82.6 mg (0. 147 mmol) of (+) 2-amino-6-benzyl-7-[1'α, 2'β-bis(benzoyloxymethyl)-cyclopropan-1'α, 2'β-yl]methylpurine obtained in Example 1, the same method as in Example 1, step 8 was carried out to obtain 27.1 mg (0.102 mmol, 69%) of (±) 7-[1'α, 2'β-bis (hydroxymethyl)cyclopropan-1'β-yl]methylguanine as a white powder; $^1$H-NMR (DMSO-d6) δ: 0.45 (dd, J=4.8, 8.7 Hz, 1H), 0.67 (dd, J=4.8, 4.8 Hz, 1H), 1.14 (m, 1H), 2.92 (dd, J=5.7, 11.7 Hz, 1H), 3.26 (dd, J=5.7, 11.7 Hz, 1H), 3.45 (ddd, J=5.4, 8.4, 11.4 Hz, 1H), 3.72 (ddd, J=5.4, 5.4, 11.4 Hz, 1H), 4.28 (d, J=14.4 Hz, 1H), 4.49 (d, J=14.4 Hz, 1H), 4.62 (dd, J=5.4, 5.4 Hz, 1H), 4.74 (dd, J=5.7, 5.7 Hz, 1H), 6.14 (broad s, 2H), 7.99 (s,1H), 10.8 (broad s, 1H); high resolution mass spectrum,
Calculated: $C_{11}H_{16}O_3N_5$ (M++H) m/z, 266.1253, Measured: m/z 266.1238.

EXAMPLE 3

Preparation of (±) 9-[1'α, 2'α-bis-(hydroxymethyl)cyclopropan-1'β-yl]methylguanine Step 1: Preparation of (E)-[1,2-bis(benzoyloxymethyl)methyl]cyclopropylmethyl p-toluene sulfonate Using 11.50 g (33.8 mmol) of (Z)-(2-benzoyloxymethyl-1-hydroxymethyl)cyclopropylmethyl benzoate obtained in Example 1, the same method as in Example 1, step 6 was carried out to obtain 15.58 g (31.5 mmol, 93%) of (E)-[1,2-bis-(benzoyloxymethyl)]cyclopropyl-methyl p-toluenesulfonate. Colorless oil; $^1$H-NMR (CDCl$_3$) δ: 0.83 (dd, J=6.0, 6.0 Hz, 1H), 107 (dd, J=6.0, 9.0 Hz, 1H), 1.5 (dddd, J=6.0, 6.0, 9.0, 9.0 Hz, 1H), 2.28 (s, 3H), 3.93 (d, J=10.5, 1H), 4.16 (dd, J=9.0, 12.0 Hz, 1H), 4.22 (d, J-12.3 Hz, 1H), 4.23 (d, J=10.5 Hz, 1H), 4.54 (d, J=12.3 Hz, 1H), 4.63 (dd, J=6.3, 12.0 Hz, 1H), 7.20 (m, 2H), 7.31 (m, 4H), 7.52 (m, 2H), 7.76 (m, 2H), 7.85 (m, 2H), 7.91 (m, 2H); FAB MASS. m/z 494 (M+).

Step 2: Preparation of (±) 2-amino-6-benzyl-9-[1'α, 2'α-bis(benzoyloxymethyl)cyclopropan-1'β-yl]methylpurine and (±) 2-amino-6-benzyl-7-[1'α, 2'α-bis(benzoyloxymethyl)cyclopropan-1'β-yl]methylpurine Using 92.1 mg (0.186 mmol) of (E)-[1,2-bis(benzoyloxymethyl)]cyclopropylmethyl p-toluenesulfonate, the same method as in Example 1, step 7 was carried out to form 64.1 mg (0.114 mmol, 61%) of (±) 2-amino-6-benzyloxy-9-[1'α, 2'α-bis(benzoyloxymethyl)cyclopropan-1'β-yl]methylpurine and 27.8 mg (0.0493 mmol, 27%) of (±) 2-amino-6-benzyloxy-7-[1'α, 2'α-bis(benzoyloxymethyl)cyclopropan-1'β-yl]methylpurine. (±) 2-Amino-6-benzyloxy-9-[1'α, 2'α-bis(benzoyloxymethyl)cyclopropan-1'β-yl]methylpurine. Colorless oil;

$^1$H-NMR(CDCl$_3$) δ: 0.87 (dd, J=6.0, 6.0 Hz, 1H), 1.29 (dd, J=5.7, 9.0 Hz, 1H), 2.02 (m, 1H), 4.10 (d, J=14.7 Hz, 1H), 4.11 (dd, J=9.6, 12.3 Hz, 1H), 4.25 (d, J=12.3 Hz, 1H), 4.30 (d, J=14.7 Hz, 1H), 4.55 (d, J=12.3 Hz, 1H), 4.72 (dd, J=6.0, 12.3 Hz, 1H), 4.92 (bs, 2H), 5.47 (s, 2H), 7.26–7.40 (m, 7H), 7.43–7.51 (m, 4H), 7.79–7.87 (m, 5H); FD MASS, m/z 563 (M+). (±) 2-Amino-6-benzyloxy-7-[1'α,2'β-bis(benzoyloxymethyl)cyclopropan-1'β-yl]methylpurine. Colorless oil: 1H-NMR (CDCl$_3$) δ: 0.81 (dd, J=6.0, 6.0 Hz, 1H), 1.06 (dd, J=6.0, 9.3 Hz, 1H), 1.82 (dddd, J=6.0, 6.0, 9.3, 9.3

Hz, 1H), 3.99 (dd, J=9.9, 12.0 Hz, 1H), 4.11 (d, J=15.0 Hz, 1H), 4.18 (d, J=12.0 Hz, 1H), 4.54 (d, J=15.0 Hz, 1H), 4.55 (d, J=12.6 Hz, 1H), 4.64 (dd, J=6.0, 12.0 Hz, 1H), 5.43 (d, J=6.0, 12.0 Hz, 1H), 5.50 (d, J=12.0 Hz, 1H), 6.21 (bs, 2H), 7.25–7.56 (m, 10H), 7.70 (m, 2H), 7.76 (m, 2H), 8.14 (s, 1H); FD MASS, m/z 563 (M+).

Step 3: Preparation of (+) 9-[j1'α, 2'α-bis(hydroxymethyl)cyclopropan-1'β-yl]-methylguanine Using 64.1 mg (0.114 mmol) of (+) 9-[1'α, 2'α-bis(hydroxymethyl)-cyclopropan-1'β-yl]methylpurine, the same method as in Example 1, step 8 was carried out to obtain 24.4 mg/0.0920 mmol, 81%) of +9-[1'α, 2'α-bis(-hydroxymethyl)-cyclopropan-1'β-yl]methyl=guanine. White powder:

$^1$H-NMR (DMSO-d6) δ: 0.40 (t, J=5.1 Hz, 1H), 0.88 (dd, J=4.8, 8.7 Hz, 1H), 1.23 (m, 1H), 3.24–3.37 (m, 2H), 3.41 (dd, J=6.0, 12.6 Hz, 1H), 3.58 (dt, J=12.0, 6.0 Hz, 1H), 3.81 (d, J=14.1 Hz, 1H), 4.00 (d, J=14.1 Hz, 1H), 4.49 (m, 1H), 4.64 (m, 1H), 6.38 (broad s, 2H), 7.71 (s, 1H), 10.49 (broad s, 1H); high resolution mass spectrum, Calculated $C_{11}H_{16}O_3N_5$ (M++H) m/z 266.1253, Measured: m/z 266.1263.

EXAMPLE 4

Preparation of (±)7-[1'α, 2'α-bis-(hydroxymethyl)cyclopropan-1'β-yl]methylguanine 124 mg (0.220 mmol) of (±)2-amino-6-benzyloxy-7-[1'α, 2'α-bis(benzyloxymethyl)-cyclopropan-1'β-yl]methylpurine obtained in Example 3, step 2 was treated with sodium methoxide as shown in Example 1, step 8 to give 44.6 mg (0.168 mmol, 76%) of (±) 7-[1'α, 2'α-bis(hydroxymethyl)cyclopropan-1'β-yl]methylguanine. This was a white powder; $^1$H-NMR(DMSO d6) δ 0.34 (t, J=5.1 Hz, 1H), 0.95 (dd, J=4.8, 8.4 Hz, 1H), 1.27 (m, 1H), 3.22–3.43 (m, 3H), 3.57 (dr, J=12.0, 6.0 Hz, 1H), 4.11 (d, J=14.1 Hz, 1H), 4.28 (d, J=14.1 Hz, 1H), 4.45 (t, J=5.1 Hz, 1H), 4.72 (t, J=5.4 Hz, 1H), 6.12 (broad s, 2H), 7.95 (s, 1H), 10.79 (broad s, 1H); high resolution mass spectrum, Calculated: $C_{11}H_{16}O_3N_5$ (M++H)m/z 266.1253, Measured: m/z 266.1241.

EXAMPLE 5

Preparation of (±)9-[1'α, 2'β-bis-(hydroxymethyl)cyclopropan-1'-β-yl]methyladenine Step 1: Preparation of (±)9-[1'α, 2'β-bis(benzyloxymethyl)cyclopropan-1β-yl]methyladenine and (±)7-[1'α, 2'β-bis-(benzyloxymethyl)cyclopropan-1'βyl]methyladenine To a suspension of 114 mg (2.85 mmol) of 60% sodium hydride (previously washed with hexane) in 18 ml of anhydrous dimethylformamide 386 mg (2.85 mmol) of adenine was added, and the mixture was stirred for 20 minutes at room temperature. Then, 1.18 g (2.38 mmol) of (Z)-[1,2-bis(benzoyloxymethyl)]cyclopropylmethyl p-toluenesulfonate obtained in Example 1 in 6 ml of anhydrous dimethylformamide was added and the mixture was stirred for 3 hours at 60° C. The solvent was distilled off, and dichloromethane and a saturated aqueous solution of sodium bicarbonate was added to the residue. The organic layer was separated, dried over anhydrous sodium sulfate and concentrated to dryness in vacuo. The resulting residue was subjected to silica gel chromatography (4–10% methanol/dichloromethane) to get 844 mg (1.84 mmol, 77%) of (±)9-[1'α, 2'β-bis-(benzoyloxymethyl)cyclopropan-1'β-yl]methyladenine and 52.8 mg (0.115 mmol), 5%) of (±)7-[1'α2'β-bis-(benzoyloxymethyl)cyclopropan-1'β-yl]methyladenine.

(±)9-[1'α, 2'β-bis(benzoyloxymethyl)cyclopropan-1'β-yl]methyladenine, white gum; $^1$H-NMR (CDCl$_3$) δ 1.06 (dd, J=5.7, 9.0 Hz, 1H), 1.26 (t, J=5.7 Hz, 1H), 1.80 (tt, 5.7, 9.0 Hz, 1H), 3.92 (d, J=12.0 Hz, 1H), 4.29–4.41 (m, 3H), 4.68 (d, J=14.7 Hz, 1H), 4.94 (dd, J=5.7, 2.3 Hz, 1H), 5.56 (bs, 2H), 7.32–7.39 (m, 4H), 7.52–7.58 (m, 2H), 7.90 (m, 2H), 7.97 (m, 2H), 8.00 (s, 1H), 8.30 (s, 1H); FD MASS, m/z 457 (M+).

(±)7-[1'α, 2'β-bis(benzoyloxymethyl)cyclopropan-1'β-yl methyladenine, white crystal; $^1$H-NMR (CDCl$_3$) δ 1.09 (t, J=6.0 Hz, 1H), 1.22 (dd, J=6.3, 9.0 Hz, 1H), 1.89 (m, 1H), 3.97 (d, J=11.7 Hz, 1H), 4.26–4.39 (m, 3H), 4.79 (dd, J=5.4, 12.6 Hz, 1H), 4.95 (d, J=15.0 Hz, 1H), 5.51 (broad s, 2H), 7.32 (m, 2H), 7.38 (m, 2H), 7.51–7.61 (m, 2H), 7.84 (m, 2H), 7.96 (m, 2H), 8.21 (s, 1H), 8.44 (s, 1H); FD MASS, m/z 457 (M+).

Step 2: Preparation of (±)9-[1'α, 2'β-bis(hydroxymethyl)cyclopropan-1'β-yl]methyladenine.

221 mg (5.53 mmol) of sodium hydride was washed with hexane and 17 ml of methanol was added. The mixture was stirred for 5 minutes at room temperature and added to 844 mg (1.85 mmol) of (±)9-[1'α, 2'β-bis(-benzoyloxymethyl)cyclopropan-1'β-yl]methyladenine. After stirring for 30 minutes at 40° C., 5.5 ml (5.5 mmol) of 1N hydrochloric acid was added. Methanol was distilled off, water added to the residue and the resultant aqueous solution was washed with ethyl acetate. The aqueous layer was evaporated to dryness and the residue was purified by reverse phase $C_{18}$ silica gel chromatography (0–30% methanol/water) to get 424 mg (1.70 mmol, 92%) of (±)9-[1'α, 2'β-bis-(hydroxymethyl)cyclopropan-1'β-yl]methyladenine as a white powder which was crystallized from methanol to obtain 389 mg (1.56 mmol, 85%) of crystalline material. White crystal; $^1$H-NMR (DMSO-d6) 6 0.53–0.60 (m, 2H), 1.14 (tt, J=6.0, 8.4 Hz 1H), 3.05 (dd, J=5.7, 11.4 Hz, 1H), 3.12 (dd, J=5.7, 11.4 Hz, 1H), 3.51 (ddd, J=5.1, 8.4, 12.0 Hz, 1H), 3.77 (ddd, J=5.1, 6.0, 11.4 Hz 1H), 4.24 (d, J=14.7 Hz, 1H), 4.32 (d, J=14.7 Hz, 1H), 4.75 (t, J=5.7 Hz, 1H), 4.84 (m, 1H), 7.19 (broad s, 2H), 8.13 (s, 1H), 8.18 (s, 1H); high resolution mass spectrum, Calculated: $C_{11}H_{16}O_2N_5$ (M++H) m/z 250.1304, Measured: m/z 250.1295.

EXAMPLE 6

Preparation of (±)7-[1'α,2'β-bis-(hydroxymethyl)cyclopropan-1'β-yl]methyladenine 52.8 mg (0.115 mmol) of (±)7-1'α, 2'β-bis(benzoyloxymethyl)cyclopropan-1'β-yl]methyladenine obtained in Example 5 was treated in the same way as shown in Example 5, step 2 to get 26.5 mg (0.106 mmol, 92%) of (±)7-[1'α, 2'β-bis-(hydroxymethyl)cyclopropan-1'β-yl]methyladenine. White powder; $^1$H-NMR (DMSO-d6) δ 0.66 (dd, J=5.1, 9.0 Hz, 1H), 0.66 (t, J=5.1 Hz, 1H), 1.18 (m, 1H), 3.02 (m, 1H), 3.13 (m, 1H), 3.50 (m, 1H), 3.74 (m, 1H), 4.36 d, J=15.0 Hz, 1H), 4.56 (d, J=15.0 Hz, 1H), 4.74 (t, J=4.8 Hz, 1H), 5.25 (broad s, 1H), 6.99 (broad s, 2H), 8.17 (s, 1H), 8.37 (s, 1H); high resolution mass spectrum, Calculated: $C_{11}H_{16}O_2N_5$ (M++H) m/z 250.1304, Measured: m/z 250.1305.

EXAMPLE 7

Preparation of (±)9-[1'α,2'α-bis-(hydroxymethyl)cyclopropan-1'β-yl]methyladenine Step 1: Preparation of (±)9-[1'α, 2'α-bis(benzoyloxymethyl)cyclopropan-1'β-yl]methyladenine and (±)7-[1'α,2'α-bis-(benzoyloxymmethyl)cyclopropan-1'β-yl]methyladenine Using 1.50 g (3.03 mmol) of (E)-[1,2-bis(benzoyloxymethyl)]cyclopropylmethyl p-toluenesulfonate obtained in Example 3 and 491 mg (3.64 mmol) of adenine, the same procedure as shown in Example 5, step 1 was carried out to obtain 1.12g (2.44 mmol, 80%) of (±)9-[1'α, 2'α-bis-(benzoyloxymethyl)cyclopropan-1'β-yl]methyladenine and 61.7 mg (0,135 mmol, 4.5%) of (±)7-[1'α, 2'α-bis(benzoyloxymethyl)cyclopropan-1'β-yl]methyladenine.

(±)9-[1'α, 2'α-bis(benzoyloxymethyl)cyclopropan-1'β-yl]methyladenine, White foam; $^1$H-NMR (CDCl$_3$) δ 0.88 (t, J=5.8 Hz, 1H), 1.36 (dd, J=5.8, 9.0 Hz, 1H), 2.03 (m, 1H), 4.11 (dd, J=9.7, 12.2 Hz, 1H), 4.23 (d, J=14.7 Hz, 1H), 4.28 (d, J=12.8 Hz, 1H), 4.39 (d, J=14.7 Hz, 1H), 4.55 (d, J=12.8 Hz, 1H) 4.71 (dd, J=5.8, 12.2 Hz, 1H), 6.04 (broad s, 2H), 7.27–7.33 (m, 4H), 7.45–7.53 (m, 2H), 7.76 (m, 2H), 7.83 (m, 2H), 7.99 (s, 1H), 8.26 (s, 1H); FD MASS, m/z 457 (M+).

(±)7-[1'α, 2'α-bis(benzoyloxymethyl)cyclopropan-1'β-yl]methyladenine. White crystal; $^1$H-NMR (CDCl$_3$) δ 0.90 (t, J=6.0 Hz, 1H), 1.12 (dd, J=6.0, 9.0 Hz, 1H), 1.69 (m, 1H), 4.16 (dd, J=9.3, 12.3 Hz, 1H), 4.36 (d, J=12.9 Hz, 1H), 4.52 (d, J=15.0 Hz, 1H), 4.58 (d, J=12.9 Hz, 1H), 4.68 (dd, J=6.0, 12.3 Hz, 1H), 5.83 (broad s, 2H), 7.31 (m, 4H), 7.45–7.54 (m, 2H), 7.83 (m, 4H), 8.10 (s, 1H), 8.34 (s, 1H); FD MASS, m/z 457 (M+).

Step 2: Preparation of (±)9-[1'α,2'α-bis(hydroxymethyl)cyclopropan-1'β-yl]methyladenine 1.12 g (2.44 mmol) of (±)9-[1'α, 2'α-bis(benzoyloxymethyl)cyclopropan-1'β-yl]methyladenine was treated in the same way as shown in Example 5, step 2 to get 489 mg (1.96 mmol, 80%) of (±)9-[1'α, 2'α-bis(-hydroxymethyl)cyclopropan-1'β-yl]methyladenine as white powder which which was crystallized from methanol to get 445 mg (1.79 mmol, 73%) of white crystalline material. $^1$H-NMR (DMSO-d6) δ 0.41 (t, J=5.1 Hz, 1H), 0.93 (dd, J=5.1, 8.7 Hz, 1H), 1.32(m, 1H), 3.23–3.44 (m, 3H), 3.58 (m, 1H), 4.02 (d, J=14.2 Hz, 1H), 4.19 (d, J=14.2 Hz, 1H), 4.56 (t, J=5.2 Hz 1H), 4.74 (t, J=5.2 Hz, 1H), 7.20 (broad s, 2H), 8.13 (s, 1H), 8.16 (s, 1H); high resolution mass spectrum, Calculated: C$_{11}$H$_{16}$O$_2$N$_5$ (M++H) m/z 250.1304, Measured: m/z 250.1310.

EXAMPLE 8

Preparation of (±)7-[1'α,2'α-bis-(hydroxymethyl)cyclopropan-1'β-yl]methyladenine 61.7 mg (0.135 mmol) of (±)7-[1'α, 2'α-bis(benzoyloxymethyl)cyclopropan-1'β-yl]methyladenine obtained in Example 7 was treated by the same procedure as in Example 5, step 2 to get 16.2 mg (0.0650 mmol, 48%) of (±)7-[1'α, 2'α-bis-(hydroxymethyl)cyclopropan-1'β-yl]methyladenine. White powder; $^1$H-NMR (DMSO-d6) δ 0.44 (t, J=5.1Hz, 1H), 0.86 (dd, J=5.1, 9.0 Hz, 1H), 1.22 (m, 1H), 3.26–3.42 (m, 3H), 3.59 (dd, J=6.3, 11.7 Hz, 1H), 4.28 (d, J=15.0 Hz, 1H), 4.40 (d, J=15.0 Hz, 1H), 4.63 (broad s, 1H), 5.12 (bs, 1H), 6.94 (broad s, 2H), 8.17 (s, 1H), 8.31 (s, 1H); high resolution mass spectrum, Calculated: C$_{11}$H$_{16}$O$_2$N$_5$ (M++H) m/z 250.1304, Measured: m/z 250.1321.

EXAMPLE 9

Preparation of (±)2-amino-6-chloro-9-[1'α,2'α-bis-(hydroxymethyl)-cyclopropan-1'β-yl]methylpurine Step 1: Preparation of (+)2-amino-6-chloro-9-[1'α,2-'α-bis(benzoyloxymethyl)cyclopropan-1'β-yl]methylpurine and (±)2-amino-6-chloro-7-[1'α, 2'α-bis-(benzoloxymethyl)cyclopropan-1'β-yl]methylpurine.

400 mg (0.809 mmol) of (E)-[1,2-bis(benzoyloxymethyl)]cyclopropylmethyl p-toluenesulfonate obtained in Example 3 was coupled with 165 mg (0.973 mmol) of 2-amino-6-chloropurine by the same method as described in Example 1, step 7 to get 323 mg (0.657 mmol, 81%) of (±)2-amino-6-chloro-9-[1'α, 2'α-bis(benzoyloxymethyl)cyclopropan-1'β-yl]methylpurine and 45.2 mg (0.0919 mmol, 11%) of (±)2-amino-6-chloro-7-[1'α, 2'α-bis-(benzoyloxymethyl)cyclopropan-1'β-yl]methylpurine.

(±)2-amino-6-chloro-9-[1'α, 2'α-bis(benzoyloxymethyl)cyclopropan-1'β-yl]methylpurine, White gum; $^1$H-NMR (CDCl$_3$) δ 0.91 (t, J=6.0 Hz, 1H), 1.26 (dd, J=6.0, 9.0 Hz, 1H), 2.04 (tt, J=6.0, 9.0 Hz, 1H), 4.02 (d, J=14.4 Hz, 1H), 4.11 (dd, J=9.0, 12.3 Hz, 1H), 4.27 (d, J=12.9 Hz, 1H), 4.32 (d, J=14.4 Hz, 1H), 4.55 (d, J=12.9 Hz, 1H), 4.74 (dd, J=6.0, 12.3 Hz, 1H), 4.91 (broad s, 2H), 7.31–7.37 (m, 4H), 7.49–7.56 (m, 2H), 7.76–7.84 (m, 4 H), 7.90 (s, 1H); FD-MASS, m/z 491 (M+).

(±)2-amino-6-chloro-7-[1'α, 2'α-bis(benzoyloxymethyl)cyclopropan-1'β-yl]methylpurine, White crystal; $^1$H-NMR (CDCl$_3$) δ 0.93 (t, J=6.0 Hz, 1H), 1.17 (dd, J=6.0, 9.3 Hz, 1H), 1.78 (tt, J=6.0, 9.3 Hz, 1H), 4.20 (dd, J=9.3, 12.3 Hz, 1H), 4.31 (d, J=12.6 Hz, 1H), 4.44 (d, J=14.7 Hz, 1H), 4.66 (d, J=12.6 Hz, 1H), 4.73 (d, J=14.7 Hz, 1H), 4.73 (m, 1H), 5.04 (broad s, 2H), 7.27–7.38 (m, 4H), 7.47–7.55 (m, 2H), 7.78 (m, 2H), 7.88 (m, 2H), 8.25 (s, 1H); FD MASS, m/z 491 (M+).

Step 2: Preparation of (±)2-amino-6-chloro-9-[1'α, 2'α-bis-hydroxymethyl)cyclopropan-1'β-yl]methylpurine 98.1 mg (0.199 mmol) of (±)2-amino-6-chloro-9-[1'α, 2'α-bis-(benzoyloxymethyl)cyclopropan-1'β-yl]methylpurine was dissolved in 14 ml of saturated ammonia in methanol and the solution was stirred for 72 hours at room temperature. After removal of the solvent the residue was dissolved in 5 ml of water and the solution was heated for 10 minutes at 100° C. The reaction mixture was then cooled, filtered and the filtrate was evaporated to dryness in vacuo. The resultant residue was crystallized from water to obtain 27.4 mg (0.0966 mmol, 49%) of (±)2-amino-6-chloro-9-[1'α, 2'α-bis(hydroxymethyl)cyclopropan-1'β-yl]methyl purine as white crystals; $^1$H-NMR (DMSO-d6) δ 0.44 (t, J=5.4 Hz, 1H), 0.92 (dd, J=5.1, 8.7 Hz, 1H), 1.31 (m, 1H), 3.31 (d, J=12.3 Hz, 1H), 3.32 (dd, J=8.7, 11.4 Hz, 1H), 3.42 (d, J=12.3 Hz, 1H), 3.61 (dd, J=6.3, 11.4 Hz, 1H), 3.99 (d, J=14.4 Hz, 1H), 4.05 (d, J=14.4 Hz, 1H), 4.54 (broad s, 1H), 4.60 (broad s, 1H), 6.85 (broad s, 2H), 8.16 (s, 1H); high resolution mass spectrum, Calculated: C$_{11}$H$_{15}$O$_2$N$_5$Cl (M++H) m/z 284.0914, Measured: m/z 284.0899.

EXAMPLE 10

Preparation of (±)2-amino-9-[1'α, 2'α-bis(hydroxymethyl)cyclopropan-1'β-yl]methylpurine Step 1: Preparation of (±) 2-amino-9-[1'α, 2'α-bis(benzoyloxymethyl)cyclopropan-1'β-yl]methylpurine 86 mg (0.081 mmol) of 10% palladium-carbon was added to a solution of 1.41 g (2.87 mmol) of (±)2-amino-6-chloro-9-[1'α, 2'α-bis(benzoyloxymethyl)cyclopropan-1'β-yl]methylpurine obtained in Example 9 and 724 mg (11.5 mmol) of ammonium formate in 29 ml of methanol and the mixture was refluxed for 3 hours at 75° C. The reaction mixture was cooled to room temperature and filtered on Celite. The filtrate was concentrated in vacuo and the residue was dissolved in water and extracted with dichloromethane. The organic layer was dried over anhydrous sodium sulfate and evaporated in vacuo. The resultant residue was purified by silica gel chromatography (4–10% methanol/dichloromethane) to get 1.10 g (2.40 mmol, 84%) of (±)2-amino-9-[1'α, 2'α-bis(benzoyloxymethyl)cyclopropan-1'β-yl]methylpurine. White gum; $^1$H-NMR (CDCl$_3$) δ 0.90 (t, J=6.0 Hz, 1H), 1.29 (dd, J=6.0, 9.3 Hz, 1H), 2.02 (tt, J=6.0, 9.3 Hz, 1H), 4.11 (d, J=14.7 Hz, 1H), 4.14 (dd, J=9.3, 12.3 Hz, 1H), 4.26 (d, J=12.9 Hz, 1H), 4.27 (d, J=14.7 Hz, 1H), 4.53 (d, J=12.9 Hz, 1H), 4.72 (dd, J=6.0, 12.3 Hz, 1H), 4.84 (broad s, 2H), 7.28–7.37 (m, 4H), 7.47, 7.56 (m, 2H), 7.80 (m, 2H), 7.88 (m, 2H), 7.89 (s, 1H), 8.57 (s, 1H); high resolution mass spectrum, Calculated: $C_{25}H_{24}O_4N_5$ (M++H) m/z 458.1829, Measured: m/z 458.1861.

Step 2: Preparation of (±)2-amino-9-[1'α, 2'α-bis(hydroxymethyl)cyclopropan-1'β-yl]methylpurine 242 mg (0.529 mmol) of (±)2-amino-9-[1'α, 2'α-bis(benzoyloxymethyl)cyclopropan-1'β-yl]methylpurine was treated by the same method as in Example 5, step 2 to get 116 mg (0.465 mmol, 88%) of (±)2-amino-9-[1'α, 2'α-bis(hydroxymethyl)cyclopropan-1'β-yl]methylpurine. White powder; $^1$H-NMR (DMSO-d6) δ 0.43 (t, J=5.1 Hz, 1H), 0.93 (dd, J=5.1, 9.0 Hz, 1H), 1.29 (m, 1H), 3.26–3.38 (m, 2H), 3.42 (dd, J=5.4, 12.0 Hz, 1H); 3.60 (m, 1H), 3.96 (d, J=14.4 Hz, 1H), 4.79 (d, J=14.4 Hz, 1H), 4.54 (t, J=5.4 Hz, 1H), 4.64 (t, J=5.4 Hz, 1H), 6.44 (broad s, 2H), 8.10 (s, 1H), 8.55 (s, 1H); high resolution mass spectrum, Calculated: $C_{11}H_{16}O_2N_5$ (M++H) m/z 250.1304, Measured: m/z 250.1316.

EXAMPLE 11

Preparation of (±) 2,6-diamino-9-[1'α, 2'α-bis(hydroxymethyl)cyclopropan-1'β-yl]methylpurine 27.4 mg (96.6 µmol) of (±)2-amino-6-chloro-9-[1'α, 2'α-bis(hydroxymethyl)cyclopropan-1'β-yl]methylpurine obtained in Example 9 was dissolved in 19 ml of saturated ammonia in methanol. The solution was stirred for 12 hours at 90° C., cooled, and concentrated in vacuo. The resultant residue was purified by a reverse phase C$_{18}$ silica gel chromatography (0.30% methanol/water) to get 12.8 mg (48.4µmol, 50%) of (±)2,6-diamino-9-[1'α, 2'α-bis(hydroxymethyl)cyclopropan-1'β-yl]methylpurine. White powder; $^1$H-NMR (DMSO-d6) δ 0.38 (t, J=5.1 Hz, 1H), 0.90 (dd, J=4.8, 8.7 Hz, 1H), 1.24 (m, 1H), 3.16–3.44 (m, 3H), 3.56 (m, 1H), 3.81 (d, J=14.4 Hz, 1H), 4.02 (d, J=14.4 Hz, 1H), 4.47 (m, H), 4.87 (m, 1H), 5.76 (broad s, 2H), 6.65 (broad s, 2H), 7.73 (s, 1H); high resolution mass spectrum, Calculated: $C_{11}H_{17}O_2N_6$ (M++H) m/z 265.1413, Measured: m/z 265.1427.

EXAMPLE 12

Preparation of (±) 9-[1'α, 2'β-bis(hydroxymethyl)cyclopropan-1'β-yl]methyl hypoxanthine To 11.7 ml of an acetic acid solution of 97.0 mg (0.389 mmol) of (±)9-[1'α,2'β-bis-(hydroxymethyl)cyclopropan-1'β-yl]methyladenine obtained in Example 5, was added 805 mg (11.7 mmol) of sodium nitrite in 3.9 ml of water. The solution was stirred for 5 hours at 60° C., cooled to room temperature, and neutralised to pH 7 by addition of 2M aqueous sodium hydroxide. After evaporation the residue was purified by a reverse phase C$_{18}$ silica gel chromatography (0–15% methanol/water) to get 86.0 mg (0.344 mmol, 88%) of (±)9-[1'α,2'β-bis-(hydroxymethyl)cyclopropan-1'β-yl]methylhypoxanthine as white powder which was crystallised from methanol to get 54.7 mg (0.219 mmol, 56%) of white crystalline material.

$^1$H-NMR(DMSO-d6)δ0.54–0.60(m,2H), 1.16(m, 1H), 3.04 (dd, J=5.1, 11.4Hz, 1H), 3.18(m, 1H), 3.48(m, 1H), 3.75(m, 1H), 4.20 (d, J=14.7Hz, 1H), 4.36 (d, J=14.7Hz, 1H), 4.61(m, 1H), 4.67 (m, 1H), 8.03 (s, 1H), 8.15 (s, 1H), 12.23 (broad s, 1H); high resolution mass spectrum, Calculated: $C_{11}H_{15}O_3N_4$ (M++H) m/z 251.1144, Measured: m/z251.1149.

EXAMPLE 13

Preparation of (±)9-[1'α, 2'α-bis-(hydroxymethyl)-cyclopropan-1'β-yl]methylhypoxanthine To 5.4 ml of acetic acid solution of 44.3 mg (0.178 mmol) of (±)9-[1'α, 2'α-bis(hydroxymethyl)cyclopropan-1'β-yl]methyladenine, obtained in Example 7, 614 mg (8.90 mmol) of sodium nitrite in 1.8 ml of water was added. The solution was stirred for 72 hours at 50° C., cooled to room temperature, and neutralized to pH 7 by addition of 2N aqueous sodium hydroxide. After evaporation the residue was purified by reverse phase C$_{18}$ silica gel chromatography (0.15% methanol/water) to get 28.2 mg (0.113 mmol, 63%) of (±)9-[1'α, 2'α-bis-(hydroxymethyl)cyclopropan-1'β-yl]methylhypoxanthine. White powder;

$^1$H-NMR (DMSO-d6) δ 0.43 (t, J=5.4 Hz, 1H), 0.90 (dd, J=4.8, 8.7 Hz 1H), 1.32 (m, 1H), 3.25–3.37 (m, 2H), 3.41 (dd, J=6.0, 12.0 Hz, 1H), 3.60 (dt, =12.0, 6.0 Hz, 1H), 4.05 (d, J=14.1 Hz, 1H), 4.17 (d, J=14.1 Hz, 1H), 4.54 (m, 1H), 4.61 (m, 1H), 8.02 (s, 1H), 8.11 (s, 1H), 12.23 (broad s, 1 H); high resolution mass spectrum, Calculated: $C_{11}H_{15}O_3N_4$ (M++H) m/z 251.1144, Measured: m/z 251.1157.

EXAMPLE 14

Preparation of (±)1-[1'α, 2'β-bis-(hydroxymethyl)cyclopropan-1'β-yl]methylthymine Step 1: Preparation of (±)1-[1'α, 2'β-bis(benzoyloxymethyl)cyclopropan-1'β-yl]methylthymine 700 mg (1.42 mmol) of (Z)-[1,2-bis(benzoyloxymethyl)]cyclopropylmethyl p-toluenesulfonate obtained in Example 1 and 215 mg (1.70 mmol) of thymine were coupled in essentially the same way as described in Example 1, step 7 to get 370 mg (0.825 mmol, 58%) of (±)1-[1'α, 2'β-bis-(benzoyloxymethyl)cyclopropan-1'β-yl]methylthymine. White gum; $^1$H-NMR (CDCl$_3$) δ 1.10 (m, 2H), 1.73 (m, 1H), 1.75 (s, 3H), 3.96 (d, J=12.0Hz, 1H), 4.04 (d, J=15.0 Hz, 1H), 4.06 (d, J=15.0 Hz 1H), 4.17 (dd, J=10.5, 12.0Hz, 1H), 4.47 (d, J=12.0 Hz, 1H), 4.86 (dd, J=5.7, 12.3 Hz, 1H), 7.13 (s, 1H), 7.27–7.38 (m, 4H), 7.51–7.57 (m, 2H), 7.92–7.99 (m, 4H), 9.16 (broad s, 1H); FD MASS, m/z 448 (M+).

Step 2: Preparation of (±) 1-[1'α, 2'β-bis(hydroxymethyl)cyclopropan-1'β-yl]methylthymine 370 mg (0.825 mmol) of (±)1-[1'α, 2'β-bis(benzoyloxymethyl)cyclopropan-1'β-yl]methylthymine was treated by the same method as shown in Example 5, step 2 to get 113 mg (0.470 mmol, 57%) of (±)1-[1'α, 2'β-bis-(hydroxymethyl)cyclopropan-1'β-yl]methylthymine. White powder; 1H-NMR (DMSO-d6) δ 0.48 (m, 1H), 0.55 (dd, J=4.5, 8.7 Hz, 1H), 1.06(m, 1H), 1.76 (d, J=0.9 Hz, 3H), 3.08 (dd, J=5.1, 11.7Hz, 1H), 3.24 (dd, J=5.7, 11.7Hz, 1H), 3.37 (m, 1H, 3.66(m, 1H), 3.77 (d, J=14.4Hz, 1H), 3.86 (d, J=14.4 Hz, 1H), 4.55–4.63 (m, 2H), 7.60 (m, 1H), 11.20 (broad s, 1H); high resolution mass spectrum, Calculated: $C_{11}H_{17}O_4N_2$ (M+ +H) m/z 241.1188, Measured: m/z 241.1193.

EXAMPLE 15

Preparation of (±)1-[1'α, 2'α-bis-(hydroxymethyl)-cyclopropan-1'β-yl]methylthymine Step 1: Preparation of (±)1-[1'α,2'α-bis-(benzolyloxymethyl)cyclopropan-1'β-yl]methylthymine 321 mg (0.649 mmol) of (E)-[1,2-bis(benzoyloxymethyl)cyclopropylmethyl p-toluenesulfonate obtained in Example 3 and 98 mg (0.777 mmol) of thymine were coupled in essentially the same way as shown in Example 1 step 7 to get 188 mg (0.419 mmol, 65%) of (±)1-[1'α, 2'α-bis(benzoyloxymethyl)cyclopropan-1'β-yl]methylthymine. White gum; 1H-NMR (CDCl3) δ 0.83 (t, J=5.7 Hz, 1H), 1.18 (dd, J=5.7, 9.0Hz, 1H), 1.70 (d, J=1.2 Hz, 1H), 1.84 (tt, J=5.7, 9.0 Hz, 1H), 3.61 (d, J=14.7 Hz, 1H), 4.08 (d, J=14.7 Hz, 1H), 4.13 (dd, J=9.0, 12.0 Hz, 1H), 4.32 (d, J=12.6 Hz, 1H), 4.64 (d, J=12.6 Hz, 1H), 4.73 (dd, J=5.7, 12.0 Hz, 1H), 7.09 (m, 1H), 7.28–7.36 (m, 4H), 7.51 (M, 2H), 7.90 (m, 4H), 8.55 (broad s, 1H); FD MASS, m/z 448 (M+).

Step 2: Preparation of (±)1-[1'α, 2'α-bis-(hydroxymethyl)cyclopropan-1'β-yl]methylthymine 188 mg (0.419 mmol) of (±)1-[1'α, 2α-bis-(benzoyloxymethyl)cyclopropan-1'β-yl]methylthymine was treated by the same method as in Example 5, step 2 to get 83.6 mg (0.348 mmol, 83%) of (±)1-[1'α,2'α-bis-(hydroxymethyl)cyclopropan-1'β-yl]methylthymine. White powder; 1H-NMR (DMSO-d6) δ 0.37 (m, 1H), 0.80 (dd, J=4.5, 8.4 Hz, 1H), 1.19 (m, 1H), 1.76 (s, 3H), 3.26–3.40 (m, 2H), 3.46–3.63 (m, 2H), 3.61 (d, J=14.1 Hz, 1H), 3.67 (d, J=14.1 Hz, 1H), 4.55 (broad s, 2H), 7.50 (s, 1H), 11.20 (broad s, 1H); high resolution mass spectrum, Calculated: $C_{11}H_{17}O_4N_2$ (M+ +H) m/z 241.1188, Measured: m/z 241.1189.

EXAMPLE 16

Preparation of (±) 1-[1'α, 2'β-bis-(hydroxymethyl)cyclopropan-1'β-yl]methylcytosine Step 1: Preparation of (±)1-[1'α, 2'β-bis(benzoyloxymethyl)cyclopropan-1'β-yl]methylcytosine 104 mg (0.210 mmol) of (Z)-[1,2-bis(benzoyloxymethyl)]cyclopropylmethyl p-toluenesulfonate obtained in Example 1 and 28 mg (0.252 mmol) of cytosine were coupled by essentially the same method as described in Example 5, step 1 to get 54.2 mg (0.125 mmol, 60%) of (±)1-[1'α, 2'β-bis-(benzoyloxymethyl)cyclopropan-1'β-yl]methylcytosine. White gum; 1H-NMR (CDCl3)δ 0.99 (dd, J=5.7, 9.0 Hz, 1H), 1.26 (t, J=5.7 Hz, 1H), 1.66 (m, 1H), 3.85 (d, J=12.0 Hz, 1H), 4.06 (d, J=15.0 Hz, 1H), 4.10 (d, J=15.0 Hz, 1H), 4.21 (dd, J=9.9, 12.3 Hz, 1H), 4.49 (d, J=12.0 Hz, 1H), 4.84 (dd, J=5.7, 12.3 Hz, 1H), 5.77 (d, J=7.2 Hz, 1H), 7.29–7.38 (m, 5H), 7.48–7.56 (m, 2H), 7.91–7.98 (m, 4H); FD MASS, m/z 434 (M+ +H).

Step 2: Preparation of (±)1-[1'α,2'β-bis(hydroxymethyl)cyclopropan-1'β-yl]methylcytosine.

93.3 mg (0.215 mmol) of (±) 1-[1'α,2'β-bis(benzoyloxymethyl)cyclopropan-1'β-yl]methylcytosine was treated by the same method as in Example 5, step 2 to get (±)1-[1'α,2'β-bis-(hydroxymethyl)cyclopropan-1'β-yl]methylcytosine. White powder; 1H-NMR (DMSO-d6) δ 0.43 (t, J=4.8 Hz, 1H), 0.49 (dd, J=4.8, 8.7 Hz, 1H), 1.02 (m, 1H), 3.02 (dd, J=6.0, 11.7 Hz, 1H), 3.10 (dd, J=6.0, 11.7 Hz, 1H), 3.38 (m, 1H), 3.65 (m, 1H), 3.76 (d, J=14.4 Hz, 1H), 3.89 (d, J=14.4 Hz, 1H), 4.71 (t, J=5.4 Hz, 1H), 4.77 (t, J=6.0 Hz, 1H), 5.68 (d, J=7.2 Hz, 1H), 7.04 (broad s, 1H), 7.09 (broad s, 1H), 7.65 (d, J=7.2 Hz, 1H); high resolution mass spectrum, Calculated: $C_{10}H_{16}O_3N_3$ (M+ +H) m/z 226.1191, Measured: m/z 226.1204.

EXAMPLE 17

Preparation of (±)1-[1'α, 2'α-bis-(hydroxymethyl)cyclopropan-1'β-yl]methylcytosine Step 1: Preparation of (±)1'α,2'α-bis-cyclopropan-1'β-yl]methylcytosine 500 mg (1.01 mmol) of (E)-[1,2-bis-(benzoyloxymethyl)]cyclopropylmethyl p-toluenesulfonate obtained in Example 3 and 135 mg (1.22 mmol) of cytosine were coupled by the same way as described in Example 5, step 1 to get 284 mg (0.655 mmol, 65%) of (±)1-[1'α, 2'α-bis-(benzoyloxymethyl)cyclopropan-1'β-yl]methylcytosine. White gum; 1H-NMR (CDCl3) δ 0.75(t, J=5.7 Hz, 1H), 1.25 (dd, J=5.7, 8.7 Hz, 1H), 1.81 (m, H), 3.81 (d, J=14.4 Hz, 1H), 4.02 (d, J=14.4 Hz, 1H), 4.16 (dd, J=9.6, 12.3 Hz, 1H), 4.28 (d, J=12.6 Hz, 1H), 4.56 (d, J=12.6 Hz, 1H), 4.62 (dd, J=6.6, 12.3 Hz, 1H), 5.68 (d, J=7.2Hz, 1H), 7.26–7.32 (m, 5H), 7.46 (m, 2H), 7.86–7.92 (m, 4H); FD MASS, m/z 434 (M+ +H).

Step 2: Preparation of (±)1-[1'α,2'α-bis-(hydroxymethyl)cyclopropan-1'β-yl]methylcytosine 284 mg (0.655 mmol) of (±) 1-[1'α, 2'α-bis-(benzoyloxymethyl)cyclopropan-1'β-yl]methylcytosine was hydrolyzed and purified by the same way as in Example 5, step 2 to get 118 mg (0.524 mmol, 80%) of (±)1-[1'α, 2'α-bis-(hydroxymethyl)cyclopropan-1'β-yl]methylcytosine. The resulting white powder was crystallised from methanol to obtain 107 mg(0.475 mmol, 73%) of white crystal. 1H-NMR (DMSO-d6) δ 0.32 (t, J=5.1Hz, 1H), 0.82 (dd, J=5.1, 9.0 Hz, 1H), 1.15 (m, 1H), 3.16–3.44 (m, 3H), 3.53 (m, 1H), 3.58 (d, J=14.1 Hz, 1H), 3.74 (d, J=14.1 Hz, 1H), 4.42 (broad s, 1H), 4.71 (t, J=5.7 Hz, 1H), 5.66 (d, J=7.2 Hz, H), 7.02 (broad s, 2H), 7.57 (d, J=7.2 Hz, 1H); high resolution mass spectrum, Calculated: $C_{10}H_{16}O_3N_3$ (M+ +H) m/z 226.1191, Measured: m/z 226.1194.

EXAMPLE 18

Preparation of (±)9-[1'α, 2'α-bis-(acetoxymethyl)cyclopropan-1'β-yl]methylguanine 106 mg (0.400 mmol) of (±)9-[1'α, 2'α-bis-(hydroxymethyl)cyclopropan-1'β-yl]methylguanine obtained in Example 3 was dissolved in 1.27 ml of anhydrous dimethylformamide, and 0.64 ml of acetic anhydride and 0.64 ml of pyridine were added. The solution was stirred for 3 hours at 75° C., cooled to room temperature, and evaporated in vacuo. The resultant residue was crystallized from methanol to obtain 99.6 mg (0.285 mmol, 71%) of (±)9-[1'α, 2'α-bis-(acetoxymethyl)cyclopropan-1'β-yl]methylguanine. White crystal; $^1$H-NMR (DMSO-d6) δ 0.71 (t, J=5.4 Hz, 1H), 1.12 (dd, J=5.4, 9.0 Hz, 1H), 1.60 (m, 1H), 1.93 (s, 3H), 1.95 (s, 3H), 3.82–3.98 (m, 5H), 4.17 (dd, J=6.6, 12.0 Hz, 1H), 6.30 (bs, 2H), 7.66 (s, 1H), 10.49 (bs, 1H); high resolution mass spectrum, Calculated: $C_{15}H_{20}O_5N_5$ (M$^+$+H) m/z 350.1465, Measured: m/z 350.1442.

EXAMPLE 19

Preparation of (±)9-[1'α, 2'α-bis-(benzoyloxymethyl)cyclopropan-1'β-yl]methylguanine To a solution of 216 mg (0.383 mmol) of (±)2-amino-6-benzyloxy-9-[1'α,2'α-bis(benzoyloxymethyl)cyclopropan-1'β-yl]methylpurine obtained in Example 3 in 3.8 ml of methanol 0.38 ml of acetic acid and 19.2 mg (0.018 mmol) of 10% palladium-carbon was added. Then the mixture was stirred for 6 hours at room temperature under hydrogen atmosphere and filterted on celite. The filtrate was concentrated and the residue was crystallized from methanol to get 88.9 mg (0.188 mmol, 49%) of (±)9-[1'α, 2'α-bis-(benzoyloxymethyl)-cyclopropan-1'β-yl]methylguanine. White cystal; $^1$H-NMR (DMSO-d6) δ 0.92 (t, J=5.7 Hz, 1H), 1.23 (dd, J=5.1, 9.0 Hz, 1H), 1.97 (m, 1H), 3.98 (d, J=14.4 Hz, 1H), 4.10 (dd, J=10.2, 12.0 Hz, 1H), 4.23 (d, J=14.4 Hz, 1H), 4.27 (d, J=12.0 Hz, 1H), 4.44 (d, J=12.0 Hz, 1H), 4.56 (dd, J=5.4, 12.0 Hz, 1H), 6.20 (broad s, 2H), 7.26 (m, 2H), 7.37 (m, 2H), 7.52 (m, 1H), 7.59 (m, 1H) 7.65(m, 2H), 7.71 (m, 2H), 7.84 (s, 1H), 10.43 (broad s, 1H); high resolution mass spectrum, Calculated: $C_{25}H_{24}O_5N_5$ (M$^+$+H) m/z 474.1778, Measured: m/z 474.1761.

EXAMPLE 20

Preparation of (−)-9-[1'S,2'R-bis(hydroxymethyl)cyclopropan-1'yl]-methylguanine

Step 1: Preparation of ethyl 3aS, 4aR)-3,3a,4,4a-tetrahydro-3-oxo-1H cyclopropa[c]furan-3a-carboxylate 2.42 g (105 mmol) of sodium was dissolved in 200 ml of ethanol under argon atmosphere at 0° C. 16.7 ml (110 mmol) of diethyl malonate was added. 7.8 ml (100 mmol) of R-(−)-epichlorohydrin (>98% ee.) in 5 ml of ethanol was added dropwise over 50 min at room temperature. The solution was heated at 75° C. for 20 h, then cooled to 0° C. and the precipiate was filtered off. The filtrate was concentrated in vacuo; water was added to the residue and the aqueous solution was extraced with dichloromethane. The organic layer was dried over anhydrous sodium sulfate and evaporated. The resultant residue was subjected to silica gel chromatography (hexane:ethyl acetate/5:1 to 1:1) to obtain 12.0 g (70 mmol, 70%) of ethyl 3aS, 4aR)-3,3a,4,4a-tetrahydro-3-oxo-1H-cyclopropa[c]furan-3a-carboxylate. Colorless oil; $^1$H-NMR (CDCl$_3$) δ 1.31 (t, J=7.1 Hz, 3H), 1.37 (dd, J=4.8, 5.4 Hz, 1H), 2.08 (dd, J=4.8, 8.0 Hz, 1H), 2.72 (m, 1H), 4.18 (d, J=9.6 Hz, 1H), 4.27 (q, J=7.1Hz, 2H), 4.36 (dd, J=4.5; 9.6 Hz, 1H); FD MASS, m/z 170 (M$^+$).

Optical purity of this compound was proved to be >98% utilizing chiral HPLC using Sumichiral OA-2500 (Sumitomo Chemicals, Osaka) (hexane: dichloroethane: ethanol/70:30:0.5)

Step 2: Preparation of ethyl (1R,2R)1,2-bis(hydroxymethyl)cyclopropanecarboxylate 12.0 g (70 mmol) of ethyl(3aS,4aR)-3,3a,4,4a-tetrahydro-3-oxo-1H-cyclopropa[c]furan-3a-carboxylate was dissolved in 200 ml of ethanol and 2.0 g (53 mmol) of sodium borohydride was added. The solution was stirred for 2 hours at room temperature and 27 ml of 2N HCl and 100 ml of ethyl acetate was added. The precipitate was filtered off and the filtrate was evaporated in vacuo Water was added to the residue and the aqueous solution was extracted with dichloromethane. The resultant organic layer was dried over anhydrous sodium sulfate and evaporated. The resultant oily residue was subjected to silica gel chromatography (dichloromethane:methanol/25:1) to obtain 8.35 g (48 mmol 69%) of ethyl 1R,2R1,2-bis(hydroxymethyl)cyclopropanecarboxylate. Colorless oil; $^1$H-NMR (CDCl$_3$) δ 0.76 (dd, J=4.8, 6.6 Hz, 1H), 1.27 (t, J=7.2 Hz, 3H), 1.49 (dd, J=4.8, 9.0 Hz, 1H), 2.05 (m, 1H), 3.23 (d, J=12.8 Hz, 1H), 3.33 (dd, J=11.1, 12.5 Hz, 1H), 4.08 (dd, J=5.1, 12.5 Hz, 1H), 4.17 (q, J=7.2 Hz, 2H), 4.52 (d, J=12.8 Hz, 1H); FD MASS, m/z 175 (M+H+).

Step 3: Preparation of ethyl (1R, 7R) -4,4-dimethyl-3,5-dioxoabicyclo[5,1,0]oct-1-yl carboxylate To a solution of 8.35 g (48 mmol) of (1R, 2R)-ethyl-1,2-bis(hydroxymethyl)cyclopropanecarboxylate in 100 ml of DMF 6 mg of p-toluenesulfonic acid monohydrate and 12 ml (100 mmol) of dimethoxypropane were added. After stirring for 12 hours at room temperature, water was added and the solution was extracted with hexane-ethyl acetate (1:1). The organic layer was washed with water and dried over anhydrous sodium sulfate, and evaporated in vacuo. The resultant residue was subjected to silica gel chromatography (hexane:ethyl acetate/5:1) to get 4.99 g (23.3 mmol, 49%) of ethyl (1R,7R)-4,4-dimethyl-3,5-dioxoabicyclo[5,1,0]oct-1-yl carboxylate. Colorless oil; $^1$H-NMR (CDCl$_3$) δ 1.28 (s, 3H)), 1.2–1.3 (m, 2H), 1.37 (s, 3H), 1.41 (dd, J=3.8, 9.5 Hz, 1H), 1.80 (m, 1H), 3.75 (d, J=13.5 Hz, 1H), 3.76 (d, J=13.2 Hz, 1H), 4.05–4.21 (m, 3H), 4.62 (d, J=13.5 Hz, 1H); FD MASS, m/z 214 (M$^+$).

Step 4: Preparation of (1S, 7R)-4,4-dimethyl-3,5-dioxabicyclo[5,1,0]oct-1-yl methanol To a solution of 7.92 g (37 mmol) of ethyl (1R,7R) 4,4-dimethyl-3,5-dioxoabicyclo[5,1,0]oct-1-yl carboxylate in dry tetrahydrofuran 20 ml of 2M lithium borohydride in tetrahydrofuran was added under argon atmosphere and the mixture was heated at 72° C. for 12 hours. After cooling to 0° C. a saturated aqueous solution of ammonium chloride was added and the mixture was extracted with ethyl acetate. The organic layer was washed with water and dried over anhydrous sodium sulfate, and evaporated to obtain 4.07 g (23.6mmol, 64%) of (1S,7R)-4,4-dimethyl-3,5-dioxabicyclo[5,1,-0]oct-1-yl methanol Colorless oil; $^1$H-NMR(CDCl$_3$) δ 0.67 (dd, J+4.4, 8.9 Hz, 1H), 0.90 (dd, J=4.4, 5.8 Hz, 1H), 1.06 (m, 1H), 1.28 (s, 3H), 1.38 (s, 3H), 3.45 (broad s, 2H),3.69 (dd, J=4.2, 13.2 Hz, 1H), 3.78 (d, J=12.9 Hz, 1H), 4.12 (dd, J=5.7, 13.2 Hz, 1H), 4.17 (dd, J=12.9 Hz, 1H); FD MASS, m/z 173 (MH+)

Step 5: Preparation of (1S, 7R)-1-benzyloxymethyl-4,4-dimethyl-3,5-dioxabicyclo[5,1,0]octane.

To a suspension of 1.2 g (30 mmol) of sodium hydride, previously washed with hexane, in 80 ml of DMF 4.07 g (23.6 mmol) of (1S,7R)-4,4-dimethyl-3,5-dioxabicyclo[5,1,0]oct-1-yl methanol was added and the mixture was stirred for 5 min. at room temperature. 3.97 ml (30 mmol) of benzyl bromide was added and the mixture was stirred for 14 hours at room temperature. Saturated aqueous solution of ammonium chloride was added and the mixture was extracted with hexane-ethyl acetate (1:1). The organic layer was washed with water and dried over anhydrous sodium sulfate, and evaporated in vacuo. The resultant residue was subjected to silica gel chromatography (hexane:ethyl acetate/5:1) to obtain 5.56 g (21.1 mmol, 90%) of (1S,7R)-1-benzyloxymethyl-4,4-dimethyl-3,5-dioxabicyclo[5,1,0]octane. Colorless oil; $^1$H-NMR(CDCl$_3$) δ 0.67 (dd, J=4.2, 8.4 Hz, 1H), 0.92 (m, 1H), 1.00 (m, 1H), 1.28 (s,3H), 1.37 (s,3H), 3.13 (d, J=10.2 Hz, 1H), 3.50 (d, J=10.2 Hz, 1H), 3.70 (dd, J=3.9, 13.2 Hz, 1H), 3.78 (d, J=13.1 Hz, 1H), 4.12 (dd, J=5.1, 13.2 Hz, 1H), 4.15 (d, J=13.1 Hz, 1H), 4.50 (d, J =12.0 Hz, 1H), 4.55 (d, J=12.0 Hz, 1H), 7.32 (m, 5H); FD MASS, m/z 262 (M+).

Step 6: Preparation of (1R,2R)-1-benzyloxymethyl-2-hydroxymethylcyclopropane-1-methanol 5.56 g (21.1mmol) of (1S, 7R)-1-benzyloxymethyl-4,4-dimethyl-3,5-dioxabicyclo[5,1,0]octane in 50 ml of tetrahydrofuran was mixed with 50 ml of 1N HCl and the mixture was stirred for 30min. at 0° C. Tetrahydrofuran was evaporated off, and the residue was extracted with dichloromethane. The organic layer was dried over anhydrous sodium sulfate and evaporated to obtain 4.08 g (18.2 mmol, 86%) of (1R,2R)-1-benzyloxymethyl-2-hydroxymethyl cyclopropane-1-methanol. Colorless oil; $^1$H-NMR(CDCl$_3$) δ: 0.41 (t, J=10.8 Hz, 1H), 0.66 (dd, J=5.4, 8.7 Hz, 1H), 1.32 (m, 1H), 3.25-3.4 (m, 4H) 3.60 (dd, J=1.7, 9.6 Hz, 1H), 4.06 (m, 1H), 4.22 (d, J=7.2 Hz, 1H), 4.27 (d, J=7.2 Hz, 1H), 4.56 (s, 2H), 7.34 (m, 5H); FD MASS, m/z 223 (MH+).

Step 7: Preparation of (1R, 2R)-2-benzoyloxymethyl-1-benzyloxymethyl cyclopropylmethyl benzoate.

To 4.08 g (18.2 mmol) of (1S,7R)-2-benzoyloxymethyl-2-hydroxymethyl cyclopropane-1-methanol in 100 ml of chloroform 11.6 ml (100mmol) of benzoyl chloride and 16.2 ml (200 mmol) of pyridine were added. After stirring for 12 hours at room temperature saturated aqueous solution of ammonium chloride was added and the mixture was extracted with dichloromethane. The organic layer was dried over anhydrous sodium sulfate and evaporated in vacuo. The resultant oily residue was subjected to silica gel chromatography (hexane:ethyl acetate/5:1) to get 5.35 g (12.4 mmol, 68%) of (1R,2R)-2-benzoyloxymethyl-1-benzyloxymethyl cyclopropylmethyl benzoate as colorless oil. $^1$H-NMR(CDCl$_3$) δ: 0.75 (t, J=5.5 Hz, 1H), 0.98 (dd, J=5.4, 9.0 Hz, 1H), 1.51 (m, 1H), 3.39 (d, J=10.1 Hz, 1H), 3.62 (d, J=10.1 Hz, 1H), 4.22 (dd, J=9.0, 12.0 Hz, 1H), 4.35 (d, J=11.9 Hz, 1H), 4.55 (s, 2H), 4.66 (dd, J=6.6, 12.0 Hz, 1H), 4.76 (d, J=11.9 Hz, 1H), 7.2–7.35 (m, 9H), 7.5 (m, 2H), 7.94 (d, J=7.2 Hz, 4H); FD MASS, m/z 430 (M+).

Step 8: Preparation of [(1S,2R)-2-benzoyloxymethyl-1-hydroxymethyl]cyclopropylmethyl benzoate.

5.35 g (12.4mmol) of (1S,2R)-2-benzoyloxymethyl-1-benzyloxymethyl)cyclopropylmethylbenzoate was dissolved in 50 ml of ethanol and 15 ml of acetic acid and 500 mg of 10%-palladium carbon was added. The mixture was stirred under hydrogen atmosphere for 3 days at room temperature. The palladium carbon was filtered off and the filtrate was evaporated to dryness. Dilute aqueous sodium hydroxide was added and the mixture was extracted with dichloromethane. The organic layer was dried over anhydrous sodium sulfate and evaporated, The resultant oil was subjected to silica gel chromatography (dichloromethane:methanol/19:1) to obtain 4.20 g (12.4 mmol, quantitative) of [(1S,2R)-2-benzoyloxymethyl-1-hydroxymethyl]cyclopropylmethyl benzoate as colorless oil. The $^1$H-NMR spectrum and FD MASS spectrum of this compound were completely identical to those of the racemic compound prepared in Example 1, step 5.

Step 9: Preparation of (1R,2R)-1,2-bis(benzoyloxymethyl)cyclopropylmethyl p-toluenesulfonate.

4.20 g (12.4 mmol) of [(1S,2R)-2-benzoyloxymethyl-1-hydroxymethyl]cyclopropylmethyl benzoate was treated in the same way as shown in Example 3, step 1 to give 5.49 g (11.1 mmol, 90%) of (1R,2R)-1,2-bis(benzoyloxymethyl)cyclopropylmethyl p-tuenesulfonate as colorless solid. The $^1$H-NMR spectrum and FD MASS spectrum of this compound were completely identical to those of the racemic compound prepared in Example 3, step 1.

Step 10: Preparation of (1'S,2'R)-2-amino-6-benzyloxy-9-[1',2'-bis(benzoyloxymethyl)cyclopropan-1'-yl]purine 800 mg (1.62 mmol) of (1R,2R)-1,2-bis(benzoyloxymethyl)cyclopropylmethyl p-toluenesulfonate was treated in the same way as shown in Example 3, step 2 to yield 616 mg (1.09 mmol, 67%) of (1'S,2'R)-2-amino-6-benzyloxy-9-[1',2'-bis(benzoyloxymethyl)cyclopropan-1'-yl]purine as colorless gum. The $^1$H-NMR spectrum and FD MASS spectrum of this compound were completely identical to those of the racemic compound prepared in Example 3, step 2.

Step 11: Preparation of (−)-9-[1'S,2'R-bis(hydroxymethyl)cyclopropane-1'yl]methylguanine.

616 mg (1.09 mmol) of (1'S,2'R)-2-amino-6-benzyloxy-9-[1',2'-bis(benzoyloxymethyl)cyclopropan-1'-yl]purine was treated in a same way as shown in Example 3, step 3 to yield 165 mg (0.62mmol, 57%) of (−)-9-[1'S,2'R-bis(hydroxymethyl)cyclopropane-1'yl]methylguanine as white powder. The $^1$H-NMR spectrum of this compound was completely identical to that of the racemic compound prepared in Example 3, step 3.

mp 285° C. (decomp), [a]$_D$(20° C.)=11° (c=0.5, DMSO), UV$_{max}$ 253 nm (ε=10500).

EXAMPLE 21

Preparation of (+)-9-[1'R, 2'S-bis(hydroxymethyl)cyclopropane-1'yl]methylguanine Optical isomer of the compound prepared in Example 20 was prepared in the same way as shown in Example 19, step 1 to 11 using S-(+)-epichlorohydrin instead of R-(−)-epichlorohydrin in step 1. The final product showed an identical absolute value of molar rotatory power to that of the optical isomer prepared in Example 19.

EXAMPLE 22

Preparation of
(1'S,2'R)-2-amino-6-chloro-9-[1',2'-bis(acetoxymethyl)-cyclopropan-1'-ly]methylpurine and
(1'S,2'R)-2-amino-6-chloro-7-[1',2'-bis(acetoxymethyl)-cyclopropane-1'-yl]methylpurine Step 1: Preparation of [(1S,2R)-2-acetoxymethyl-1-benzyloxymethyl]cyclopropylmethyl acetate.

662 mg (2.98mmol) of [(1R,2R)-2-benzyloxymethyl-2-hydroxymethyl]cyclopropane-1-methanol obtained in Example 20, step 6 and 1.12 ml (11.9 mmol) of acetic anhydride were treated in essentially the same way as shown in Example 20, step 7 to get 772 mg (2.52 mmol, 85%) of [(1S,2S)-2-acetoxymethyl-1-benzyloxymethyl]-cyclopropylmethyl acetate. Colorless oil; $^1$H-NMR(CDCl$_3$) δ 0.59 (t, J=5.4 Hz, 1H), 0.85 (dd, J=5.4, 8.7 Hz, 1H), 1.28 (m, 1H), 2.02 (s, 3H), 2.05 (s, 3H), 3.28 (d, J=9.9 Hz, 1H), 3.43 (d, J=9.9 Hz, 1H), 4.02 (dd, J=8.1, 12.0 Hz, 1H), 4.06 (d, J=12.0 Hz, 1H), 4.21 (dd, J=6.9, 12.0 Hz, 1H), 4.38 (d, J=12.0 Hz, 1H), 4.51 (s, 2H), 7.27–7.37 (m, 5H); FD MASS, m/z 306 (M+).

Step 2: Preparation of [(1S,2R)-2-acetoxymethyl-1-hydroxymethyl]cyclopropylmethyl acetate.

138 mg (0.450 mmol) of [(1S,2R)-2-acetoxymethyl-1benzyloxymethyl]cyclopropylmethylacetate was treated by the same method as described in Example 20, step 8 to obtain 87.5 mg (0.405 mmol, 90%) of [(1S,2R)-2-acetoxymethyl-1-hydroxymethyl]cyclopropylmethyl acetate as colorless oil. $^1$H-NMR(CDCl$_3$) 0.59 (t, J=5.4 Hz, 1H), 0.86 (dd, J=5.4, 8.7 Hz, 1H), 1.29 (m, 1H), 2.06 (s, 3H), 2.09 (s, 3H), 3.37 (dd, J=6.6, 11.7 Hz, 1H), 3.52 (dd, J=6.0, 11.7 Hz, 1H), 4.02 (dd, J=8.1, 12.0 Hz, 1H), 4.06 (d, J=12.3 Hz, 1H), 4.23 (dd, J=6.9, 12.0 Hz, 1H), 4.42 (d, J=12.3 Hz, 1H); FAB MASS, m/z 217 (M++H).

Step 3: Preparation of [(1R,2R)-1,2-bis(acetoxymethyl)]cyclopropylmethyl p-toluenesulfonate 87.5 mg (0.405 mmol) of [(1S,2R)-2-acetoxymethyl-1-hydroxymethyl]cyclopropylmethyl acetate was treated in the same way as shown in Example 3, step 1 to give 147 mg (0.397 mmol, 98%) of [(1R,2R)-1,2-bis(acetoxymethyl)]cyclopropylmethyl p-toluenesulfonate as colorless oil. $^1$H-NMR(CDCl$_3$) 0.66 (t, J=6.0 Hz, 1H), 0.89 (dd, J=6.0, 9.0 Hz, 1H), 1.31 (m, 1H), 1.97 (s, 3H), 2.03 (s, 3H), 2.45 (s, 3H), 3.85 (d, J=10.5 Hz, 1H), 3.92 (dd, J=8.4, 12.3 Hz, 1H), 3.95 (d, J=12.0 Hz, 1H), 4.00 (d, J=10.5 Hz, 1H), 4.20 (dd, J=6.9, 12.0 Hz, 1H), 4.21 (d, J=12.0 Hz, 1H), 7.35 (m, 2H), 7.78 (m, 2H); FAB MASS, m/z 371 (M++H).

Step 4: Preparation of (1'S,2'R)-2-amino-6-chloro-9-[1',2'-bis(acetoxymethyl)cyclopropan-1'-ly]methylpurine and (1'S,2'R)-2-amino-6-chloro-7-[1',2'-bis(acetoxymethyl)cyclopropane-1'-yl]methylpurine 147 mg (0.397mmol, 85%) of [(1R,2R)-1,2-bis(acetoxymethyl)]cyclopropylmethyl p-toluenesulfonate was treated by the same method as described in Example 3, step 2 to get 124 mg (0.337 mmol, 85%) of (1'S,2'R)-2-amino-6-chloro-9-[1',2'-bis(acetoxymethyl)cyclopropan-1'-ly]methylpurine and 21.9 mg (0.0596 mmol, 15%) of (1'S,2'R)-2-amino-6-chloro-7-[1',2'-bis(acetoxymethyl)cyclopropane-1'-yl]methylpurine.

(1'S,2'R)-2-amino-6-chloro-9-[1',2'-bis(acetoxymethyl)cyclopropan-1'-yl]methylpurine; colorless oil; $^1$H-NMR(CDCl$_3$) 0.73 (t, J=6.0 Hz, 1H), 1.15 (dd, J=6.0, 9.0 Hz, 1H), 1.77 (m, 1H), 1.97 (s, 3H), 1.98 (s, 3H), 3.88 (dd, J=9.0, 12.0 Hz, 1H), 3.91 (d, J=14.4 Hz, 1H), 3.96 (d, J=12.6 Hz, 1H), 4.17 (d, J=12.6 Hz, 1H), 4.20 (d, J=14.4, 1H), 4.33 (dd, J=6.6, 12.0 Hz, 1H), 5.13 (bs, 2H), 7.87 (s, 1H); high resolution mass spectrum, Calculated: C$_{15}$H$_{19}$O$_4$N$_5$Cl(M++H) m/z 368.1126, Measured: m/z 368.1127. (1'S,2'R)-2-amino-6-chloro-7-[1',2'-bis(acetoxymethyl)cyclopropane-1'-yl]methylpurine, white crystalline solid; $^1$H-NMR(CDCl$_3$) 0.78 (t, J=6.0 Hz, 1H), 1.06 (dd, J=6.0, 9.0 Hz, 1H), 1.53 (tt, J=6.0, 9.0 Hz, 1H), 1.98 (s, 3H), 2.04 (s, 3H), 3.90 (dd, J=9.0, 12.3 Hz, 1H), 4.00 (d, J=12.9 Hz, 1H), 4.21 (d, J=12.9 Hz, 1H), 4.27 (d, J=15.0 Hz, 1H), 4.37 (dd, J=6.0, 12.3 Hz, 1H), 4.64 (d, J=15.0 Hz, 1H), 5.13 (bs, 2H), 8.18 (s, 1H); high resolution mass spectrum, Calculated: C$_{15}$H$_{19}$O$_4$N$_5$Cl(M++H) m/z 368.1126, Measured: m/z 368.1126.

EXAMPLE 23

Anti-viral Activity

Anti-herpes activity was measured in a plaque-reduction assay (Lopez, C. et al., J. Antimicrob. Agents Chemother., 17, 803 (1980). Confluent monolayers of Vero cells in 6-well plates were infected with 100 plaque forming units of either HSV-1 (strain KOS) or HSV-2 (strain 186). The infected monolayers were incubated at 37° C. for 1 hour and then overlaid with maintenance medium containing 1% agarose and various concentrations of test compounds. The monolayers were incubated for a further 7 days at 37° C., after which the cells were fixed and stained, the plaques were counted, and the concentration of compound causing 50% inhibition of plaque formation was calculated. IC$_{50}$ values are shown in Table 1.

TABLE 1

| | Antiviral Activity of the Cyclopropane Derivatives | | |
|---|---|---|---|
| | | ID$_{50}$ (μg/ml) | |
| Example No. | Structure | HSV-1 | HSV-2 |
| Acyclovir | | 0.57 | 0.40 |
| 1. | (±) structure | 10.4 | |
| 3. | (±) structure | 0.046 | 0.42 |

TABLE 1-continued

Antiviral Activity of the Cyclopropane Derivatives

| Example No. | Structure | ID$_{50}$ (μg/ml) | |
|---|---|---|---|
| | | HSV-1 | HSV-2 |
| 7. | (±) 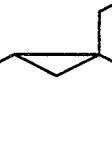 | 47.0 | |
| 9. | (±) 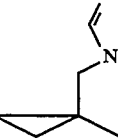 | 34.0 | |
| 16. | (±) 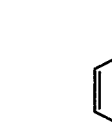 | 120 | |
| 20. | (−) 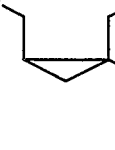 | 0.023 | 0.24 |
| 21. | (+) 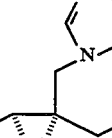 | 2.2 | |

We claim:

1. A cyclopropane of the formula (I)

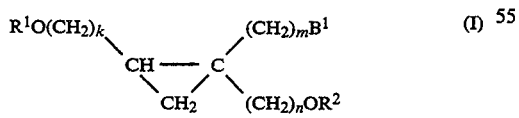

having antiherpes viral activity, wherein $B^1$ is a purine residue selected from the group consisting of guanine, adenine, 2-amino-6-chloropurine, 2-aminopurine, 2,6-diaminopurine, xanthine and 2-amino-6-alkoxypurine, $R^1$ and $R^2$ are, independently hydrogen or a hydroxyl protecting group and each of k, m and n is, independently, an integer of 1 or 2, or a pharmaceutically acceptable salt thereof.

2. A cyclopropane according to claim 1 wherein each of k, m and n is 1.

3. A cyclopropane according to claim 1 wherein each of $R^1$ and $R^2$ is hydrogen.

4. A cyclopropane according to claim 1 wherein $B^1$ is a purin-7-yl or purine-9-yl group.

5. A cyclopropane according to claim 4 wherein $B^1$ is a purine residue selected from guanine of formula (II), adenine of formula (III), 2-amino-6-chloropurine of formula (IV), 2-aminopurine of formula (V), 2,6 diamino purine of formula (VI), xanthine of formula (VII) and hypoxanthine of formula (VIII)

(II)
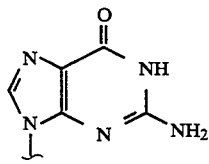

(III)
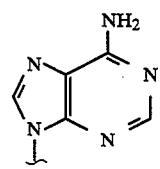

(IV)
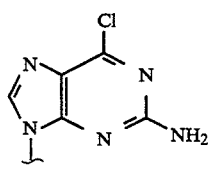

(V)
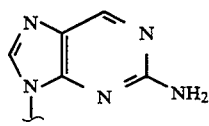

(VI)
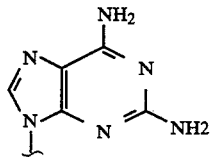

(VII)
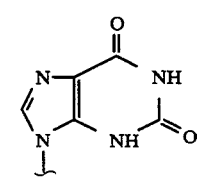

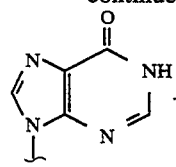 (VIII)

6. A cyclopropane according to claim 1 wherein the cyclopropane moiety has a 1S, 2R configuration as shown in formula (XII)

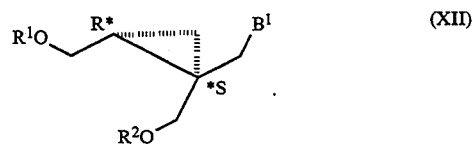 (XII)

7. A cyclopropane according to claim 1 wherein the cyclopropane moiety has 1R, 2S configuration as shown in formula (XIII)

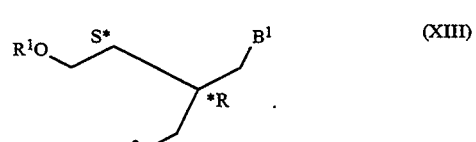 (XIII)

8. The compound of claim 1, wherein $B^1$ is a purin-9-yl.

9. The compound of claim 1, wherein $B^1$ is guanin-9-yl.

10. 9-[1'α,2'α-bis(hydroxymethyl)cyclopropan-1'β-yl]methylguanine or pharmaceutically acceptable salt thereof.

11. (−)-9-[1',2'α-bis(hydroxymethyl)cyclopropan-1'β-yl]methylguanine or pharmaceutically acceptable salt thereof.

12. A pharmaceutical composition comprising an antiherpes viral effective amount of a cyclopropane or salt of claim 1 and a pharmaceutically acceptable excipient diluent or carrier.

13. A method of treating herpes viral infections comprising administering to a human in need of such treatment an antiherpes viral effective amount of a compound of claim 1.

* * * * *

UNITED STATES PATENT AND TRADEMARK OFFICE
CERTIFICATE OF CORRECTION

PATENT NO. : 5,342,840
DATED : AUGUST 30, 1994
INVENTOR(S) : SATOSHI HATSUYA ET AL

It is certified that error appears in the above-indentified patent and that said Letters Patent is hereby corrected as shown below:

Column 31, Example No. 21., delete in its entirety and replace with

--21.    (+)    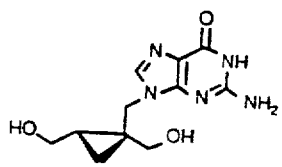    2.2 --

Column 34, delete lines 24-29 and replace with

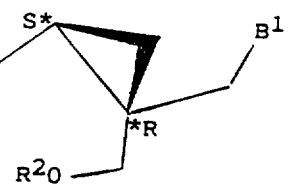    (XIII) --

Signed and Sealed this

Sixth Day of June, 1995

Attest:

BRUCE LEHMAN

Attesting Officer          Commissioner of Patents and Trademarks